(12) United States Patent
Huang et al.

(10) Patent No.: US 7,786,347 B2
(45) Date of Patent: Aug. 31, 2010

(54) INHIBITOR OF APOPTOSIS PROTEINS AND NUCLEIC ACIDS AND METHODS FOR MAKING AND USING THEM

(75) Inventors: Qihong Huang, San Diego, CA (US); John C. Reed, Rancho Santa Fe, CA (US); Bruce D. Hammock, Davis, CA (US); Quinn L. Deveraux, San Diego, CA (US); Susumu Maeda, Pasadena, CA (US); Hiroko Maeda, legal representative, Pasadena, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 80 days.

(21) Appl. No.: 11/623,637

(22) Filed: Jan. 16, 2007

(65) Prior Publication Data

US 2007/0218507 A1 Sep. 20, 2007

Related U.S. Application Data

(63) Continuation of application No. 10/041,859, filed on Jan. 7, 2002, now Pat. No. 7,172,880.

(60) Provisional application No. 60/260,478, filed on Jan. 8, 2001.

(51) Int. Cl.
*C12N 15/82* (2006.01)
*A01H 5/00* (2006.01)
*A01H 5/10* (2006.01)

(52) U.S. Cl. .................. 800/279; 800/288; 800/298; 800/301

(58) Field of Classification Search .................. None
See application file for complete search history.

(56) References Cited

U.S. PATENT DOCUMENTS 6,570,069 B1 * 5/2003 Hammock et al. .......... 800/298
7,172,880 B2 * 2/2007 Huang et al. ............... 435/69.1

FOREIGN PATENT DOCUMENTS

WO   WO 98/53091    11/1998
WO   WO 99 /47689    9/1999
WO   WO 00/26391  *  5/2000

OTHER PUBLICATIONS

Van Camp W. et al. Enhancement of oxidative stress tolerance in transgenic tobacco plants overproducing Fe-superoxide dismutase in chloroplasts. Plant Physiol. Dec. 1996; 112(4): 1703-14.*
Tamura T. et al. Osmotic stress tolerance of transgenic tobacco expressing a gene encoding a membrane-located receptor-like protein from tobacco plants. Plant Physiol. Feb. 2003;131(2):454-62.*
Mittler R. et al. Inhibition of Programmed Cell Death in Tobacco Plants during a Pathogen-Induced Hypersensitive Response at Low Oxygen Pressure. Plant Cell. Nov. 1996;8(11):1991-2001.*
Cellini F. et al. Food Chem. Toxicol. Jul. 2004; 42 (7): 1089-1125.*
Day P.R. Am. J. Clin. Nutr. Apr. 1996; 63 (4): 651S-656S.*
Ayliffe M. A. et al. Mol. Plant Microbe Interact. Aug. 2004; 17 (8): 853-864.*
Abraham M.C. et al. Trends Cell Biol. Apr. 2004; 14 (4): 184-193.*
Huang et al. Biochim. Biophys. Acta. Jan. 15, 2001; 1499 (3): 191-198.*
Huang Q, Deveraux QL, Maeda S, Salvesen GS, Stennicke HR, Hammock BD, Reed JC. Evolutionary conservation of apoptosis mechanisms: lepidopteran and baculoviral inhibitor of apoptosis proteins are inhibitors of mammalian caspase-9.Proc Natl Acad Sci U S A. Feb. 15, 2000;97(4):1427-32.
Tambunan J, Kan Chang P. Li H, Natori M. Molecular cloning of a cDNA encoding a silkworm protein that contains the conserved BH regions of BcI-2 family proteins.Gene. Jun. 8, 1998;212(2):287-93.
Seshagiri S, Vucic D, Lee J, Dixit VM. Baculovirus-based genetic screen for antiapoptotic genes identifies a novel IAP. J Biol Chem. Dec. 17, 1999;274(51):36769-73.
Huang Q, Deveraux QL, Maeda S, Stennicke HR, Hammock BD, Reed JC. Cloning and characterization of an inhibitor of apoptosis protein (IAP) from Bombyx mori.Biochim Biophys Acta. Jan. 15, 2001;1499(3):191-8.

* cited by examiner

*Primary Examiner*—Cynthia Collins
(74) *Attorney, Agent, or Firm*—Arnall Golden Gregory LLP; Robert A. Hodges

(57) ABSTRACT

The invention provides polypeptides comprising inhibitor of apoptosis protein (IAP) family members, such as BmIAP initially derived from *Bombyx mori* BmN cells, and nucleic acids encoding them, and methods for making and using these compositions, including their use for inhibiting apoptosis.

22 Claims, 4 Drawing Sheets

| | | Occlusion body formation |
|---|---|---|
| A  | BmIAP | + |
| B  | BmIAP-BIR | -- |
| C  | BmIAP-RING | -- |
| D  | SfIAP | + |
| E  | AcIAP | -- |
| F  | mock transfection | N/A |

SEQUENCE LISTING

```
<160> NUMBER OF SEQ ID NOS: 27

<210> SEQ ID NO 1
<211> LENGTH: 3773
<212> TYPE: DNA
<213> ORGANISM: Bombyx mori
<220> FEATURE:
<221> NAME/KEY: CDS
<222> LOCATION: (2733)..(3770)

<400> SEQUENCE: 1
cattattaaa ctcacttcac ttcggtagtg tgaatgttaa cgtgaaactc cgcgctcttc      60
tttagttgct actcggttct gtctggctgc gttgacgttt tggaacttca tactattttg     120
ttcttgcaag acgagtgtca gtgattaaac aaaaacataa gaatagacgt tttatgcgtt     180
actaaaaaaa aggaaaaata taccaatgga gttgacgaaa gttgctaaaa atggagctgc     240
cgccacgttg gtgatgttaa aaaatgcgcg ggatgcaaaa atgcgacctt tcattggtcc     300
gctcatgtta tcctcgtgtg agtcttcaac gacatccaca ctcccgtcac cttcgtcgtc     360
agctgataaa acggataatc acgacacatt caacttcctt cctgatatgc ccgacatgcg     420
tcgtgaagag gaacgtctga aaacatttga tcagtggccc gttacgtttt tgacgccgga     480
acaattggcc cgcaacggat tctactacct cggtcgcggc gacgaagtgt gctgtgcttt     540
ctgtaaggta gaaattatga ggtgggtcga aggcgacgat cctgccgccg atcatcggag     600
atgggcgccc cagtgtccct ttgtacgaaa acaaatgtat gccaacgctg ggggagaggc     660
gaccgctgtc ggtagagacg aatgtggggc cagtgcggcc acgcagcctc cccgcatgcc     720
cggccccgtg cacgcgcggt actccaccga ggccgcgcgg ctcgccacct tcaaggactg     780
gccgagacgt atgcgccaaa aacccgagga actggcagag gccggattct tctatacagg     840
ccaaggtgac aaaacgaaat gcttctattg cgacggaggg ctaaaagatt gggaaagcga     900
tgacgttccg tgggaacagc acgccagatg gttcgaccgc tgcgcgtacg tgcaattggt     960
gaaaggacgt gactacattc agaaggtgaa gtcggaggcc actgcgatat ctgctagcga    1020
agaagaacag gccgccacca atgattcgac taagaacgtc gcccaagagg gcgagaaaca    1080
```

-continued

```
tttggatgac tctaaaatat gtaaaatatg ttattccgag gagcgtaacg tgtgcttcgt    1140
gccgtgcggc cacgtggtgg cgtgcgccaa gtgcgcgctg tcgacggaca agtgcccgat    1200
gtgtcgcagg acgttcacga atgcggtgcg gctctacttc tcgtgaaagg accctcctcg    1260
cgagctgtat actaatcact tcaccgggcg gccctggagc gtgctgaaac caccccttcga   1320
acgaaaccgc gtatcctgtg atttttacat taaataaatt tacaaattga tagcggtggg    1380
gcaatgtata ggaactcgtc agaactcgcg agttgacgtg caggaaggag ttagtgattt    1440
gtaaacttgt aaactgatgt tgaaatgatt ttatttatta tttaaaattc taatgacaaa    1500
gtgtaagtaa ataaatgtac atattatttt agattatcag tttgtcccac cgacaaaagt    1560
gaaatgtaca taggtgtttt catatcactt caacagtcga agaccttctt tttgaattta    1620
aggatatata tttatacata taaattaaaa ttttaacgag acatcaatat aaatggttta    1680
acaacttatt tatacactga aatcaagtga agtgtaacat ggtctgaaga atgttttact    1740
gatttcactt cccctgttga agtgataaaa ttctaatgta aatccagagt ttaaatgtcg    1800
tcataattaa tataagaaac aagttttacg cttcttttgc ttgaaaaatc ttataattga    1860
ttcaggaatt atttaatgtg actatatttt gttcctgtaa ataacataat atatactatt    1920
tattgattaa ttctgacata atttatggca attccgtaag atacaatcca atacttattt    1980
catgtaactc acttcaaaat agttgaatgt gtggtgtgat tataatgtta aatgtctaaa    2040
tttataataa attgagcaaa gttgcattta atgtatgaat actaattatt gttttaacaa    2100
aacatttaag tataatctgc tctgtgattt taatgtatca agaaataacc ccaacacctt    2160
aattgaagtt tttacattgt tgctgataaa aaaaatcata tcaattacat ttacaagtca    2220
attttaattg ttcagaaacc aaacacaatt ttgttagtga ctcctgcttt acgaagtagt    2280
atgacaaacc agtgtttcgt tgattgcatt aatttagttg taaccaatat ttacactcaa    2340
cattttaaga tgtcattgag gaattctgta taaaaaatgg gaatttatttt attggtgtat   2400
aatacaatcc cgcacaagcc atttgcaagt ttctacacaa ctaaaacgta ttgtatccat    2460
tatctatacg tcatatcatt aatatatact tgctttagca aacatatatt cacgaataac    2520
ttcacaatat attttttgtaa atcaacatat taatggtaat taacgaatcg cacggtacaa   2580
atagtgataa ctgctgagtg cactaaatag taagagaatt tatttaaaca gtcaaatttt    2640
gtttcataag tagttatttc atactgttga atgttattca ttaaaacaaa tgttaaagca    2700
aaaaaaaaaa aaaaagtcg tgactgggaa aa atg gag ttg acg aaa gtt gct       2753
                                   Met Glu Leu Thr Lys Val Ala
                                    1               5 aaa aat gga gct gcc gcc acg ttg gtg atg tta aaa aat gcg cgg gat      2801
Lys Asn Gly Ala Ala Ala Thr Leu Val Met Leu Lys Asn Ala Arg Asp
         10                  15                  20 gca aaa atg cga cct ttc att ggt ccg ctc atg tta tcc tcg tgt gag      2849
Ala Lys Met Arg Pro Phe Ile Gly Pro Leu Met Leu Ser Ser Cys Glu
     25                  30                  35 tct tca acg aca tcc aca ctc ccg tca cct tcg tcg tca gct gat aaa      2897
Ser Ser Thr Thr Ser Thr Leu Pro Ser Pro Ser Ser Ser Ala Asp Lys
 40                  45                  50                  55 acg gat aat cac gac aca ttc aac ttc ctt cct gat atg ccc gac atg      2945
Thr Asp Asn His Asp Thr Phe Asn Phe Leu Pro Asp Met Pro Asp Met
                 60                  65                  70 cgt cgt gaa gag gaa cgt ctg aaa aca ttt gat cag tgg ccc gtt acg      2993
Arg Arg Glu Glu Glu Arg Leu Lys Thr Phe Asp Gln Trp Pro Val Thr
             75                  80                  85
```

```
ttt ttg acg ccg gaa caa ttg gcc cgc aac gga ttc tac tac ctc ggt    3041
Phe Leu Thr Pro Glu Gln Leu Ala Arg Asn Gly Phe Tyr Tyr Leu Gly
         90                  95                 100 cgc ggc gac gaa gtg tgc tgt gct ttc tgt aag gta gaa att atg agg    3089
Arg Gly Asp Glu Val Cys Cys Ala Phe Cys Lys Val Glu Ile Met Arg
    105                 110                 115 tgg gtc gaa ggc gac gat cct gcc gcc gat cat cgg aga tgg gcg ccc    3137
Trp Val Glu Gly Asp Asp Pro Ala Ala Asp His Arg Arg Trp Ala Pro
120                 125                 130                 135 cag tgt ccc ttt gta cga aaa caa atg tat gcc aac gct ggg gga gag    3185
Gln Cys Pro Phe Val Arg Lys Gln Met Tyr Ala Asn Ala Gly Gly Glu
                140                 145                 150 gcg acc gct gtc ggt aga gac gaa tgt ggg gcc agt gcg gcc acg cag    3233
Ala Thr Ala Val Gly Arg Asp Glu Cys Gly Ala Ser Ala Ala Thr Gln
            155                 160                 165 cct ccc cgc atg ccc ggc ccc gtg cac gcg cgg tac tcc acc gag gcc    3281
Pro Pro Arg Met Pro Gly Pro Val His Ala Arg Tyr Ser Thr Glu Ala
        170                 175                 180 gcg cgg ctc gcc acc ttc aag gac tgg ccg aga cgt atg cgc caa aaa    3329
Ala Arg Leu Ala Thr Phe Lys Asp Trp Pro Arg Arg Met Arg Gln Lys
    185                 190                 195 ccc gag gaa ctg gca gag gcc gga ttc ttc tat aca ggc caa ggt gac    3377
Pro Glu Glu Leu Ala Glu Ala Gly Phe Phe Tyr Thr Gly Gln Gly Asp
200                 205                 210                 215 aaa acg aaa tgc ttc tat tgc gac gga ggg cta aaa gat tgg gaa agc    3425
Lys Thr Lys Cys Phe Tyr Cys Asp Gly Gly Leu Lys Asp Trp Glu Ser
                220                 225                 230 gat gac gtt ccg tgg gaa cag cac gcc aga tgg ttc gac cgc tgc gcg    3473
Asp Asp Val Pro Trp Glu Gln His Ala Arg Trp Phe Asp Arg Cys Ala
            235                 240                 245 tac gtg caa ttg gtg aaa gga cgt gac tac att cag aag gtg aag tcg    3521
Tyr Val Gln Leu Val Lys Gly Arg Asp Tyr Ile Gln Lys Val Lys Ser
        250                 255                 260 gag gcc act gcg ata tct gct agc gaa gaa gaa cag gcc gcc acc aat    3569
Glu Ala Thr Ala Ile Ser Ala Ser Glu Glu Glu Gln Ala Ala Thr Asn
    265                 270                 275 gat tcg act aag aac gtc gcc caa gag ggc gag aaa cat ttg gat gac    3617
Asp Ser Thr Lys Asn Val Ala Gln Glu Gly Glu Lys His Leu Asp Asp
280                 285                 290                 295 tct aaa ata tgt aaa ata tgt tat tcc gag gag cgt aac gtg tgc ttc    3665
Ser Lys Ile Cys Lys Ile Cys Tyr Ser Glu Glu Arg Asn Val Cys Phe
                300                 305                 310 gtg ccg tgc ggc cac gtg gtg gcg tgc gcc aag tgc gcg ctg tcg acg    3713
Val Pro Cys Gly His Val Val Ala Cys Ala Lys Cys Ala Leu Ser Thr
            315                 320                 325 gac aag tgc ccg atg tgt cgc agg acg ttc acg aat gcg gtg cgg ctc    3761
Asp Lys Cys Pro Met Cys Arg Arg Thr Phe Thr Asn Ala Val Arg Leu
        330                 335                 340 tac ttc tcg tga                                                    3773
Tyr Phe Ser
    345

<210> SEQ ID NO 2
<211> LENGTH: 346
<212> TYPE: PRT
<213> ORGANISM: Bombyx mori

<400> SEQUENCE: 2

Met Glu Leu Thr Lys Val Ala Lys Asn Gly Ala Ala Ala Thr Leu Val
  1               5                  10                  15
```

```
Met Leu Lys Asn Ala Arg Asp Ala Lys Met Arg Pro Phe Ile Gly Pro
             20                  25                  30

Leu Met Leu Ser Ser Cys Glu Ser Ser Thr Thr Ser Thr Leu Pro Ser
         35                  40                  45

Pro Ser Ser Ser Ala Asp Lys Thr Asp Asn His Asp Thr Phe Asn Phe
     50                  55                  60

Leu Pro Asp Met Pro Asp Met Arg Arg Glu Glu Glu Arg Leu Lys Thr
 65                  70                  75                  80

Phe Asp Gln Trp Pro Val Thr Phe Leu Thr Pro Glu Gln Leu Ala Arg
                 85                  90                  95

Asn Gly Phe Tyr Tyr Leu Gly Arg Gly Asp Glu Val Cys Cys Ala Phe
            100                 105                 110

Cys Lys Val Glu Ile Met Arg Trp Val Glu Gly Asp Asp Pro Ala Ala
        115                 120                 125

Asp His Arg Arg Trp Ala Pro Gln Cys Pro Phe Val Arg Lys Gln Met
    130                 135                 140

Tyr Ala Asn Ala Gly Gly Glu Ala Thr Ala Val Gly Arg Asp Glu Cys
145                 150                 155                 160

Gly Ala Ser Ala Ala Thr Gln Pro Pro Arg Met Pro Gly Pro Val His
                165                 170                 175

Ala Arg Tyr Ser Thr Glu Ala Ala Arg Leu Ala Thr Phe Lys Asp Trp
            180                 185                 190

Pro Arg Arg Met Arg Gln Lys Pro Glu Glu Leu Ala Glu Ala Gly Phe
        195                 200                 205

Phe Tyr Thr Gly Gln Gly Asp Lys Thr Lys Cys Phe Tyr Cys Asp Gly
    210                 215                 220

Gly Leu Lys Asp Trp Glu Ser Asp Asp Val Pro Trp Glu Gln His Ala
225                 230                 235                 240

Arg Trp Phe Asp Arg Cys Ala Tyr Val Gln Leu Val Lys Gly Arg Asp
                245                 250                 255

Tyr Ile Gln Lys Val Lys Ser Glu Ala Thr Ala Ile Ser Ala Ser Glu
            260                 265                 270

Glu Glu Gln Ala Ala Thr Asn Asp Ser Thr Lys Asn Val Ala Gln Glu
        275                 280                 285

Gly Glu Lys His Leu Asp Asp Ser Lys Ile Cys Lys Ile Cys Tyr Ser
    290                 295                 300

Glu Glu Arg Asn Val Cys Phe Val Pro Cys Gly His Val Val Ala Cys
305                 310                 315                 320

Ala Lys Cys Ala Leu Ser Thr Asp Lys Cys Pro Met Cys Arg Arg Thr
                325                 330                 335

Phe Thr Asn Ala Val Arg Leu Tyr Phe Ser
            340                 345

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: a, c, g or t
```

```
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (12)
<223> OTHER INFORMATION: a, c, g or t

<400> SEQUENCE: 3
gcngangcng gnttyttyta                                                   20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (15)
<223> OTHER INFORMATION: a, c, g or t

<400> SEQUENCE: 4
acnacrtgnc crcangg                                                      17

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgttcccac ggaacgtc                                                     18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccaccaatg attcgac                                                      17

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic
      conserved motif
<220> FEATURE:
<221> NAME/KEY: MOD_RES
<222> LOCATION: (2)..(3)
<223> OTHER INFORMATION: Variable residue
<220> FEATURE:
<221> NAME/KEY: MOD_RES
<222> LOCATION: (5)..(10)
```

```
<223> OTHER INFORMATION: Variable residue
<220> FEATURE:
<221> NAME/KEY: MOD_RES
<222> LOCATION: (12)..(20)
<223> OTHER INFORMATION: Variable residue
<220> FEATURE:
<221> NAME/KEY: MOD_RES
<222> LOCATION: (22)..(27)
<223> OTHER INFORMATION: Variable residue

<400> SEQUENCE: 7

Cys Xaa Xaa Cys Xaa Xaa Xaa Xaa Xaa Trp Xaa Xaa Xaa Xaa Xaa
 1               5                  10                  15

Xaa Xaa Xaa Xaa His Xaa Xaa Xaa Xaa Xaa Cys
                20                  25

<210> SEQ ID NO 8
<211> LENGTH: 172
<212> TYPE: PRT
<213> ORGANISM: Bombyx mori

<400> SEQUENCE: 8

Glu Glu Glu Arg Leu Lys Thr Phe Asp Gln Trp Pro Val Thr Phe Leu
 1               5                  10                  15

Thr Pro Glu Gln Leu Ala Arg Asn Gly Phe Tyr Tyr Leu Gly Arg Gly
                20                  25                  30

Asp Glu Val Cys Cys Ala Phe Cys Lys Val Glu Ile Met Arg Trp Val
             35                  40                  45

Glu Gly Asp Asp Pro Ala Ala Asp His Arg Arg Trp Ala Pro Gln Cys
         50                  55                  60

Pro Phe Val Glu Ala Ala Arg Leu Ala Thr Phe Lys Asp Trp Pro Arg
 65                  70                  75                  80

Arg Met Arg Gln Lys Pro Glu Glu Leu Ala Glu Ala Gly Phe Phe Tyr
                 85                  90                  95

Thr Gly Gln Gly Asp Lys Thr Lys Cys Phe Tyr Cys Asp Gly Gly Leu
            100                 105                 110

Lys Asp Trp Glu Ser Asp Asp Val Pro Trp Glu Gln His Ala Arg Trp
        115                 120                 125

Phe Asp Arg Cys Ala Tyr Val Leu Cys Lys Ile Cys Tyr Ser Glu Glu
    130                 135                 140

Arg Asn Val Cys Phe Val Pro Cys Gly His Val Val Ala Cys Ala Lys
145                 150                 155                 160

Cys Ala Leu Ser Thr Asp Lys Cys Pro Met Cys Arg
                165                 170

<210> SEQ ID NO 9
<211> LENGTH: 172
<212> TYPE: PRT
<213> ORGANISM: Spodoptera frugiperda

<400> SEQUENCE: 9

Glu Asp Glu Arg Met Lys Thr Phe Glu Lys Trp Pro Val Ser Phe Leu
 1               5                  10                  15

Ser Gly Glu Gln Leu Ala Arg Asn Gly Phe Tyr Tyr Leu Gly Arg Arg
                20                  25                  30

Asp Glu Ala Arg Cys Ala Phe Cys Lys Val Glu Ile Met Arg Trp Val
             35                  40                  45

Glu Gly Asp Asp Pro Ala Lys Asp His Gln Arg Trp Ala Pro Gln Cys
         50                  55                  60
```

```
Pro Phe Val Glu Ala Ala Arg Leu Arg Ser Phe Lys Asp Trp Pro Arg
 65                  70                  75                  80

Cys Met Arg Gln Lys Pro Glu Glu Leu Ala Glu Ala Gly Phe Phe Tyr
                 85                  90                  95

Thr Gly Gln Gly Asp Lys Thr Lys Cys Phe Tyr Cys Asp Gly Gly Leu
            100                 105                 110

Lys Asp Trp Glu Asn His Asp Val Pro Trp Glu Gln His Ala Arg Trp
        115                 120                 125

Phe Asp Arg Cys Ala Tyr Val Leu Cys Lys Ile Cys Tyr Ala Glu Glu
    130                 135                 140

Arg Asn Val Cys Phe Val Pro Cys Gly His Val Val Ala Cys Ala Lys
145                 150                 155                 160

Cys Ala Leu Ala Ala Asp Lys Cys Pro Met Cys Arg
                165                 170

<210> SEQ ID NO 10
<211> LENGTH: 172
<212> TYPE: PRT
<213> ORGANISM: Trichoplusia ni

<400> SEQUENCE: 10

Glu Asp Glu Arg Ile Lys Thr Phe Glu Lys Trp Pro Val Ser Phe Leu
 1               5                  10                  15

Ser Gly Glu Gln Leu Ala Arg Asn Gly Phe Tyr Tyr Leu Gly Arg Gly
            20                  25                  30

Asp Glu Val Arg Cys Ala Phe Cys Lys Val Glu Ile Met Arg Trp Val
        35                  40                  45

Glu Gly Asp Asp Pro Ala Lys Asp His Gln Arg Trp Ala Pro Gln Cys
 50                  55                  60

Pro Phe Val Glu Ala Ala Arg Leu Arg Ser Phe Lys Asp Trp Pro Arg
 65                  70                  75                  80

Cys Met Arg Gln Lys Pro Glu Glu Leu Ala Glu Ala Gly Phe Phe Tyr
                 85                  90                  95

Thr Gly Gln Gly Asp Lys Thr Lys Cys Phe Tyr Cys Asp Gly Gly Leu
            100                 105                 110

Lys Asp Trp Glu Asn Asp Val Pro Trp Glu Gln His Ala Arg Trp
        115                 120                 125

Phe Asp Arg Cys Ala Tyr Val Leu Cys Lys Ile Cys Phe Ala Glu Glu
    130                 135                 140

Arg Asn Val Cys Phe Val Pro Cys Gly His Val Val Ala Cys Ala Lys
145                 150                 155                 160

Cys Ala Leu Ala Ala Asp Lys Cys Pro Met Cys Arg
                165                 170

<210> SEQ ID NO 11
<211> LENGTH: 172
<212> TYPE: PRT
<213> ORGANISM: Cydia pomonella granulovirus

<400> SEQUENCE: 11

Glu Asp Val Arg Leu Asn Thr Phe Glu Lys Trp Pro Val Ser Phe Leu
 1               5                  10                  15

Ser Pro Glu Thr Met Ala Lys Asn Gly Phe Tyr Tyr Leu Gly Arg Ser
            20                  25                  30

Asp Glu Val Arg Cys Ala Phe Cys Lys Val Glu Ile Met Arg Trp Lys
        35                  40                  45
```

```
Glu Gly Glu Asp Pro Ala Ala Asp His Lys Lys Trp Ala Pro Gln Cys
 50                  55                  60

Pro Phe Val Glu Ala Ala Arg Val Lys Ser Phe His Asn Trp Pro Arg
 65                  70                  75                  80

Cys Met Lys Gln Arg Pro Glu Gln Met Ala Asp Ala Gly Phe Phe Tyr
                 85                  90                  95

Thr Gly Tyr Gly Asp Asn Thr Lys Cys Phe Cys Asp Gly Gly Leu
            100                 105                 110

Lys Asp Trp Glu Pro Glu Asp Val Pro Trp Glu Gln His Val Arg Trp
            115                 120                 125

Phe Asp Arg Cys Ala Tyr Val Leu Cys Lys Ile Cys Tyr Val Glu Glu
            130                 135                 140

Cys Ile Val Cys Phe Val Pro Cys Gly His Val Val Ala Cys Ala Lys
145                 150                 155                 160

Cys Ala Leu Ser Val Asp Lys Cys Pro Met Cys Arg
            165                 170
```

<210> SEQ ID NO 12
<211> LENGTH: 172
<212> TYPE: PRT
<213> ORGANISM: Orgyia pseudotsugata

<400> SEQUENCE: 12

```
Lys Ala Ala Arg Leu Gly Thr Tyr Thr Asn Trp Pro Val Gln Phe Leu
  1               5                  10                  15

Glu Pro Ser Arg Met Ala Ala Ser Gly Phe Tyr Tyr Leu Gly Arg Gly
                 20                  25                  30

Asp Glu Val Arg Cys Ala Phe Cys Lys Val Glu Ile Thr Asn Trp Val
            35                  40                  45

Arg Gly Asp Asp Pro Glu Thr Asp His Lys Arg Trp Ala Pro Gln Cys
 50                  55                  60

Pro Phe Val Glu Ala Ala Arg Leu Arg Thr Phe Ala Glu Trp Pro Arg
 65                  70                  75                  80

Gly Leu Lys Gln Arg Pro Glu Glu Leu Ala Glu Ala Gly Phe Phe Tyr
                 85                  90                  95

Thr Gly Gln Gly Asp Lys Thr Arg Cys Phe Cys Cys Asp Gly Gly Leu
            100                 105                 110

Lys Asp Trp Glu Pro Asp Asp Ala Pro Trp Gln Gln His Ala Arg Trp
            115                 120                 125

Tyr Asp Arg Cys Glu Tyr Val Leu Cys Lys Ile Cys Leu Gly Ala Glu
            130                 135                 140

Lys Thr Val Cys Phe Val Pro Cys Gly His Val Val Ala Cys Gly Lys
145                 150                 155                 160

Cys Ala Ala Gly Val Thr Thr Cys Pro Val Cys Arg
            165                 170
```

<210> SEQ ID NO 13
<211> LENGTH: 172
<212> TYPE: PRT
<213> ORGANISM: Drosophila melanogaster

<400> SEQUENCE: 13

```
Glu Glu Thr Arg Leu Lys Thr Phe Thr Asp Trp Pro Leu Asp Trp Leu
  1               5                  10                  15

Asp Lys Arg Gln Leu Ala Gln Thr Gly Met Tyr Phe Thr His Ala Gly
                 20                  25                  30
```

Asp Lys Val Lys Cys Phe Phe Cys Gly Val Glu Ile Gly Cys Trp Glu
            35                  40                  45

Gln Glu Asp Gln Pro Val Pro Glu His Gln Arg Trp Ser Pro Asn Cys
 50                  55                  60

Pro Leu Leu Glu Thr Ala Arg Leu Arg Thr Phe Glu Ala Trp Pro Arg
 65                  70                  75                  80

Asn Leu Lys Gln Lys Pro His Gln Leu Ala Glu Ala Gly Phe Phe Tyr
                85                  90                  95

Thr Gly Val Gly Asp Arg Val Arg Cys Phe Ser Cys Gly Gly Gly Leu
            100                 105                 110

Met Asp Trp Asn Asp Asn Asp Glu Pro Trp Glu Gln His Ala Leu Trp
            115                 120                 125

Leu Ser Gln Cys Arg Phe Val Leu Cys Lys Ile Cys Tyr Gly Ala Glu
        130                 135                 140

Tyr Asn Thr Ala Phe Leu Pro Cys Gly His Val Val Ala Cys Ala Lys
145                 150                 155                 160

Cys Ala Ser Ser Val Thr Lys Cys Pro Leu Cys Arg
                165                 170

<210> SEQ ID NO 14
<211> LENGTH: 68
<212> TYPE: PRT
<213> ORGANISM: Bombyx mori

<400> SEQUENCE: 14

Glu Ala Ala Arg Leu Ala Thr Phe Lys Asp Trp Pro Arg Arg Met Arg
 1               5                  10                  15

Gln Lys Pro Glu Glu Leu Ala Glu Ala Gly Phe Phe Tyr Thr Gly Gln
                20                  25                  30

Gly Asp Lys Thr Lys Cys Phe Tyr Cys Asp Gly Gly Leu Lys Asp Trp
            35                  40                  45

Glu Ser Asp Asp Val Pro Trp Glu Gln His Ala Arg Trp Phe Asp Arg
 50                  55                  60

Cys Ala Tyr Val
 65

<210> SEQ ID NO 15
<211> LENGTH: 68
<212> TYPE: PRT
<213> ORGANISM: Spodoptera frugiperda

<400> SEQUENCE: 15

Glu Ala Ala Arg Leu Arg Ser Phe Lys Asp Trp Pro Arg Cys Met Arg
 1               5                  10                  15

Gln Lys Pro Glu Glu Leu Ala Glu Ala Gly Phe Phe Tyr Thr Gly Gln
                20                  25                  30

Gly Asp Lys Thr Lys Cys Phe Tyr Cys Asp Gly Gly Leu Lys Asp Trp
            35                  40                  45

Glu Asn His Asp Val Pro Trp Glu Gln His Ala Arg Trp Phe Asp Arg
 50                  55                  60

Cys Ala Tyr Val
 65

<210> SEQ ID NO 16
<211> LENGTH: 68
<212> TYPE: PRT
<213> ORGANISM: Trichoplusia ni -continued

<400> SEQUENCE: 16

Glu Ala Ala Arg Leu Arg Ser Phe Lys Asp Trp Pro Arg Cys Met Arg
1               5                   10                  15

Gln Lys Pro Glu Glu Leu Ala Glu Ala Gly Phe Phe Tyr Thr Gly Gln
            20                  25                  30

Gly Asp Lys Thr Lys Cys Phe Tyr Cys Asp Gly Gly Leu Lys Asp Trp
        35                  40                  45

Glu Asn Asp Asp Val Pro Trp Glu Gln His Ala Arg Trp Phe Asp Arg
    50                  55                  60

Cys Ala Tyr Val
65

<210> SEQ ID NO 17
<211> LENGTH: 68
<212> TYPE: PRT
<213> ORGANISM: Cydia pomonella granulovirus

<400> SEQUENCE: 17

Glu Ala Ala Arg Val Lys Ser Phe His Asn Trp Pro Arg Cys Met Lys
1               5                   10                  15

Gln Arg Pro Glu Gln Met Ala Asp Ala Gly Phe Phe Tyr Thr Gly Tyr
            20                  25                  30

Gly Asp Asn Thr Lys Cys Phe Tyr Cys Asp Gly Gly Leu Lys Asp Trp
        35                  40                  45

Glu Pro Glu Asp Val Pro Trp Glu Gln His Val Arg Trp Phe Asp Arg
    50                  55                  60

Cys Ala Tyr Val
65

<210> SEQ ID NO 18
<211> LENGTH: 68
<212> TYPE: PRT
<213> ORGANISM: Orgyia pseudotsugata

<400> SEQUENCE: 18

Glu Ala Ala Arg Leu Arg Thr Phe Ala Glu Trp Pro Arg Gly Leu Lys
1               5                   10                  15

Gln Arg Pro Glu Glu Leu Ala Glu Ala Gly Phe Phe Tyr Thr Gly Gln
            20                  25                  30

Gly Asp Lys Thr Arg Cys Phe Cys Cys Asp Gly Gly Leu Lys Asp Trp
        35                  40                  45

Glu Pro Asp Asp Ala Pro Trp Gln Gln His Ala Arg Trp Tyr Asp Arg
    50                  55                  60

Cys Glu Tyr Val
65

<210> SEQ ID NO 19
<211> LENGTH: 68
<212> TYPE: PRT
<213> ORGANISM: Drosophila melanogaster

<400> SEQUENCE: 19

Glu Thr Ala Arg Leu Arg Thr Phe Glu Ala Trp Pro Arg Asn Leu Lys
1               5                   10                  15

Gln Lys Pro His Gln Leu Ala Glu Ala Gly Phe Phe Tyr Thr Gly Val
            20                  25                  30

Gly Asp Arg Val Arg Cys Phe Ser Cys Gly Gly Gly Leu Met Asp Trp
        35                  40                  45

```
Asn Asp Asn Asp Glu Pro Trp Glu Gln His Ala Leu Trp Leu Ser Gln
         50                  55                  60

Cys Arg Phe Val
 65

<210> SEQ ID NO 20
<211> LENGTH: 37
<212> TYPE: PRT
<213> ORGANISM: Bombyx mori

<400> SEQUENCE: 20

Leu Cys Lys Ile Cys Tyr Ser Glu Glu Arg Asn Val Cys Phe Val Pro
  1               5                  10                  15

Cys Gly His Val Val Ala Cys Ala Lys Cys Ala Leu Ser Thr Asp Lys
             20                  25                  30

Cys Pro Met Cys Arg
         35

<210> SEQ ID NO 21
<211> LENGTH: 37
<212> TYPE: PRT
<213> ORGANISM: Spodoptera frugiperda

<400> SEQUENCE: 21

Leu Cys Lys Ile Cys Tyr Ala Glu Glu Arg Asn Val Cys Phe Val Pro
  1               5                  10                  15

Cys Gly His Val Val Ala Cys Ala Lys Cys Ala Leu Ala Ala Asp Lys
             20                  25                  30

Cys Pro Met Cys Arg
         35

<210> SEQ ID NO 22
<211> LENGTH: 37
<212> TYPE: PRT
<213> ORGANISM: Trichoplusia ni

<400> SEQUENCE: 22

Leu Cys Lys Ile Cys Phe Ala Glu Glu Arg Asn Val Cys Phe Val Pro
  1               5                  10                  15

Cys Gly His Val Val Ala Cys Ala Lys Cys Ala Leu Ala Ala Asp Lys
             20                  25                  30

Cys Pro Met Cys Arg
         35

<210> SEQ ID NO 23
<211> LENGTH: 37
<212> TYPE: PRT
<213> ORGANISM: Cydia pomonella granulovirus

<400> SEQUENCE: 23

Leu Cys Lys Ile Cys Tyr Val Glu Glu Cys Ile Val Cys Phe Val Pro
  1               5                  10                  15

Cys Gly His Val Val Ala Cys Ala Lys Cys Ala Leu Ser Val Asp Lys
             20                  25                  30

Cys Pro Met Cys Arg
         35

<210> SEQ ID NO 24
<211> LENGTH: 37
<212> TYPE: PRT
```

```
<213> ORGANISM: Orgyia pseudotsugata

<400> SEQUENCE: 24

Leu Cys Lys Ile Cys Leu Gly Ala Glu Lys Thr Val Cys Phe Val Pro
  1               5                  10                  15
Cys Gly His Val Val Ala Cys Gly Lys Cys Ala Ala Gly Val Thr Thr
             20                  25                  30
Cys Pro Val Cys Arg
         35

<210> SEQ ID NO 25
<211> LENGTH: 37
<212> TYPE: PRT
<213> ORGANISM: Drosophila melanogaster

<400> SEQUENCE: 25

Leu Cys Lys Ile Cys Tyr Gly Ala Glu Tyr Asn Thr Ala Phe Leu Pro
  1               5                  10                  15
Cys Gly His Val Val Ala Cys Ala Lys Cys Ala Ser Ser Val Thr Lys
             20                  25                  30
Cys Pro Leu Cys Arg
         35

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      fluorogenic caspase-9 substrate

<400> SEQUENCE: 26

Leu Glu His Asp
  1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      fluorogenic caspase-3 substrate

<400> SEQUENCE: 27

Asp Glu Val Asp
  1
```

INHIBITOR OF APOPTOSIS PROTEINS AND NUCLEIC ACIDS AND METHODS FOR MAKING AND USING THEM

PRIORITY INFORMATION

This application is a continuation of application Ser. No. 10/041,859, filed Jan. 7, 2002 now U.S. Pat. No. 7,172,880, entitled "Inhibitor of Apoptosis Proteins and Nucleic Acids and Methods for Making and Using Them", by Huang et al., which claims priority to U.S. Provisional Application Ser. No. 60/260,478, filed Jan. 8, 2001. The aforementioned applications are hereby incorporated herein by reference in their entirety.

STATEMENT AS TO RIGHTS TO INVENTIONS MADE UNDER FEDERALLY SPONSORED RESEARCH

This invention was made with Government support under National Institutes of Health grants ES02701, AG15402, ES 04699, CA30199 (NCI); U.S. Department of Agriculture grants 97-35302-4406, 9802852; Binational Agriculture Research and Development grant 96-34339-3532; and, National Institutes of Environmental Health Science grant ES 05705. The Government has certain rights in the invention.

TECHNICAL FIELD

This invention generally pertains to the fields of cell biology and molecular biology. In particular, this invention provides polypeptides comprising the inhibitor of apoptosis protein (IAP) family member BmIAP, initially derived from silkworm *Bombyx mori* BmN cells, and nucleic acids encoding them, and methods for making and using these compositions, including their use for inhibiting caspase proteases and apoptosis.

BACKGROUND

Apoptosis or programmed cell death is a cellular suicide process in which damaged or harmful cells are eliminated from multicellular organisms. Cells undergoing apoptosis have distinct morphological changes including cell shrinkage, membrane blebbing, chromatin condensation, apoptotic body formation and fragmentation. This cell suicide program is evolutionarily conserved across animal and plant species. Apoptosis plays an important role in the development and homeostasis of metazoans and is also critical in insect embryonic development and metamorphosis. Furthermore, apoptosis acts as a host defense mechanism. For example, virally infected cells are eliminated by apoptosis to limit the propagation of viruses. Apoptosis mechanisms are involved in plant reactions to biotic and abiotic insults. Dysregulation of apoptosis has been associated with a variety of human diseases including cancer, neurodegenerative disorders and autoimmune diseases. Accordingly, identification of novel mechanisms to manipulate apoptosis provides new means to study and manipulate this process.

The first "inhibitor of apoptosis protein" (IAPs) was identified in a baculovirus. The baculovirus IAPs, CpIAP and OpIAP, are able to block apoptosis induced by p35-deficient baculovirus AcMNPV in insect Sf-21 cells. Cellular IAP homologues have been found in various animal species including worms, insects and humans. IAP proteins have a distinctive primary structure. They contain one to three copies of "baculoviral IAP repeat" (BIR) domain and most IAPs also contain a RING domain near their C-termini. The BIR domain contains a highly conserved arrangement of Cys/His residues forming a stable fold that chelates zinc. The BIR region was also found to interact with regulators of IAPs including Grim, Reaper and Hid from *Drosophila* and may also mediate homo-oligomerization. The RING finger is a common zinc-binding motif that also exists in other cellular proteins. Recent studies show that several IAPs, including XIAP (a NF-kappaB-dependent member of the IAP gene family, see, e.g., Deveraux (1999) EMBO J. 18:5242-5251), cIAP1, CIAP2, DIAP1, SfIAP and CpIAP are inhibitors of caspases, a family of intracellular proteases responsible for the execution of the apoptosis program. These IAPs can directly bind and inhibit some members of caspase family including caspases-3, -7 and -9. Structure-function studies have demonstrated that inhibition of caspases-3 and -7 requires only a single BIR domain while RING domain may perform other functions including recruitment of ubiquitin conjugating enzymes (UBCs). When expressed without the associated BIRs, the RING region of SfIAP was found to enhance the proapoptotic activity of mammalian caspase-9 suggesting this domain operates as a trans-dominant inhibitor of endogenous proteins involved in apoptosis suppression. Ectopic expression of lepidopteran SfIAP and baculoviral CpIAP blocks apoptosis in mammalian cells, suggesting conservation of the apoptosis program among various species and a shared mechanism used by the IAP family.

*Bombyx mori* (silkworm) has been domesticated for silk-production for thousands of years. Used together with baculoviruses, it has also been developed as an organism for large-scale production of foreign proteins in the biotechnology industry. Despite its extensive use in sericulture and biotechnology, to date no apoptosis-regulating genes of silkworm have been identified.

SUMMARY

The invention provides an isolated or recombinant nucleic acid comprising a nucleic acid sequence having at least about 95% sequence identity, about 97% sequence identity, about 99% sequence identity to SEQ ID NO:1. In one aspect of the invention, the nucleic acid encodes a polypeptide capable of inhibiting apoptosis in insect cells, encodes a polypeptide capable of inhibiting apoptosis in insect cells, such as lepidopteran and coleopteran cells, e.g., *Bombyx mori* or *Spodoptera frugiperda* cells. In one aspect the nucleic acid encodes a polypeptide capable of inhibiting apoptosis in mammalian cells, encodes a polypeptide capable of inhibiting apoptosis in plant cells, or encodes a polypeptide capable of inhibiting caspase 9, e.g., human caspase 9. In others aspects, the isolated or recombinant nucleic acid encodes a polypeptide having a sequence as set forth in SEQ ID NO:2, and, comprises a nucleic acid sequence as set forth in SEQ ID NO:1.

The invention provides an expression cassette (e.g., vector, recombinant virus) comprising at least one nucleic acid of the invention operably linked to a promoter. The nucleic acid can comprise a sequence having at least 95% sequence identity to SEQ ID NO:1. As defined herein, in one aspect, an expression cassette comprises a nucleic acid of the invention operably linked to a promoter. The promoter can be a constitutive or an inducible promoter, or, the promoter can be a developmentally regulated or a tissue specific promoter. In one aspect, the nucleic acid on the expression cassette encodes a polypeptide having a sequence as set forth in SEQ ID NO:2.

The invention provides a transformed cell comprising a nucleic acid of the invention. This nucleic acid can comprise a sequence having at least 95% sequence identity to SEQ ID NO:1. The cell can be a mammalian cell (such as a human cell), an insect cell, such as a *Spodoptera frugiperda* or *Bombyx mori* cell, a plant cell, a bacteria, a yeast cell, and the like. The transformed cell can comprise a nucleic acid encoding a polypeptide having a sequence as set forth in SEQ ID NO:2. These transformed cells can be used in the screening methods of the invention, which provide for identification of modulators of the polypeptides of the invention, or, compositions that specifically bind to the polypeptides of the invention.

The invention provides a non-human transgenic animal comprising a nucleic acid sequence of the invention, e.g., one having at least 95% sequence identity to SEQ ID NO:1. The nonhuman transgenic animal can be a rat or a mouse. The nonhuman transgenic animal can comprise a nucleic acid encoding a polypeptide having a sequence as set forth in SEQ ID NO:2. The nucleic acid can encode a polypeptide capable of inhibiting apoptosis.

The invention provides a transgenic plant comprising a nucleic acid sequence of the invention, e.g., one having at least 95% sequence identity to SEQ ID NO:1. The transgenic plant can comprise a nucleic acid encoding a polypeptide capable of inhibiting apoptosis. The transgenic plant, as a result of expression of the nucleic acid of the invention, can become abiotic or biotic insult resistant. The biotic insult can be induced by a plant pathogen, such as a virus, a fungus, a bacteria or a nemotode. The abiotic insult can be induced by high moisture, low moisture, salinity, nutrient deficiency, air pollution, high temperature, low temperature, soil toxicity, herbicides or insecticides. The transgenic plant, upon expressing a nucleic acid of the invention or being exposed to a polypeptide of the invention, can be phenotypically altered, e.g., wherein at least a portion of the plant exhibits a decreased level of senescence. The invention provides a seed capable of germinating into a plant having in its genome a heterologous nucleic acid sequence comprising a nucleic acid of the invention, e.g., one having at least 95% sequence identity to SEQ ID NO:1. The seed can comprise a nucleic acid encoding a polypeptide capable of inhibiting apoptosis in a plant cell.

The invention provides an isolated or recombinant polypeptide comprising a sequence having at least 95% sequence identity to SEQ ID NO:2. The isolated or recombinant polypeptide of the invention can be capable of inhibiting apoptosis in cells, e.g., in insect cells, such as lepidopteran cells, e.g., *Bombyx mori* or *Spodoptera frugiperda* cells, and coleopteran cells, in mammalian cells, in yeast cells, in bacterial cells, in plant cells. In one aspect, the isolated or recombinant polypeptide of the invention is capable of inhibiting caspase 9. The invention provides an isolated or recombinant polypeptide comprising a sequence as set forth in SEQ ID NO:2.

The invention provides a fusion protein comprising a polypeptide of the invention, e.g., a sequence having at least 95% sequence identity to SEQ ID NO:2, and a second domain. The fusion protein's second domain can comprise glutathione S-transferase (GST), and other domains, as described below.

The invention provides an antibody or binding fragment thereof, wherein the antibody or fragment specifically binds to a polypeptide or an immunogenic fragment thereof, wherein the polypeptide comprises a sequence having at least 95% sequence identity to SEQ ID NO:2. The invention provides an antibody or binding fragment thereof, wherein the antibody or fragment specifically binds to a protein having an amino acid sequence as set forth in SEQ ID NO:2 or an immunogenic fragment thereof.

The invention provides an array comprising a nucleic acid comprising a nucleic acid of the invention, e.g., a sequence having at least 95% sequence identity to SEQ ID NO:1, or, a fragment thereof.

The invention provides a method of detecting or isolating a polypeptide, wherein the polypeptide comprises a sequence having at least 95% sequence identity to SEQ ID NO:2, comprising contacting a biological sample with an antibody as set forth in claim 38 or claim 39. The invention provides a method of making a recombinant polypeptide comprising expressing a nucleic acid comprising a sequence having at least 95% sequence identity to SEQ ID NO:1.

The invention provides a method for inhibiting apoptosis in a cell comprising the following steps: (a) providing an isolated or recombinant polypeptide comprising a sequence having at least 95% sequence identity to SEQ ID NO:2, wherein the polypeptide is capable inhibiting apoptosis in the cell, and, (a) contacting the polypeptide with the cell in an amount sufficient to inhibit apoptosis in the cell. The invention provides a method for inhibiting apoptosis in a cell comprising the following steps: (a) providing an isolated or recombinant nucleic acid comprising a sequence having at least 95% sequence identity to SEQ ID NO:1, wherein the nucleic acid encodes polypeptide capable of inhibiting apoptosis in the cell, and, (b) contacting the nucleic acid with the cell and expressing the nucleic acid to produce an amount of polypeptide sufficient to inhibit apoptosis in the cell. In alternative aspects of these methods the cell can be an insect cell, e.g., a lepidopteran cell, such as a *Bombyx mori* cell or a *Spodoptera frugiperda* cell, and a coleopteran cell, a mammalian cell, or a plant cell.

The invention provides a method for identifying an agent that can modulate the activity of a polypeptide, wherein the polypeptide comprises a sequence having at least 95% sequence identity to SEQ ID NO:2 and is capable inhibiting a caspase 9 protease, comprising: (a) providing an isolated or recombinant polypeptide comprising a sequence having at least 95% sequence identity to SEQ ID NO:2 that is capable inhibiting a caspase 9 protease, and a test agent, (b) contacting the caspase 9 protease and polypeptide in the presence and absence of the test agent; and, (c) measuring the ability of the polypeptide to inhibit the caspase 9 protease in the presence and absence of the test agent, wherein an increase or decrease in the ability of the polypeptide to inhibit the caspase 9 protease in the presence of the test agent identifies the test agent as a modulator of the polypeptide's activity.

The invention provides a method for identifying an agent that can modulate the activity of a polypeptide, wherein the polypeptide comprises a sequence having at least 95% sequence identity to SEQ ID NO:2 and is capable inhibiting apoptosis in a cell, comprising: (a) contacting a cell expressing the polypeptide recombinantly in the presence and absence of a test agent before, during or after inducing apoptosis in the cell; and, (b) measuring the amount or degree of the polypeptide's activity in the cell in the presence and absence of the test agent, wherein an increase or decrease in the amount or degree of apoptosis in the cell in the presence of the test agent identifies the test agent as a modulator of the polypeptide's activity, In alternative aspects of these methods the cell can be an insect cell, e.g., a lepidopteran cell, such as a *Bombyx mori* cell or a *Spodoptera frugiperda* cell, or a coleopteran cell, a mammalian cell, a yeast cell, a bacterial cell, a plant cell, and the like. The degree of the polypeptide's activity in the cell can be determined by measuring the amount or degree of apoptosis in the cell; the amount or degree of caspase protease activity in the cell; the amount or degree of DNA fragmentation in the cell; the amount or degree of cleavage of substrates of caspases in the cell; or by measuring the amount or degree of any surrogate marker of apoptosis in the cell.

The invention provides a method of generating an abiotic or biotic insult-resistant plant comprising the following steps: (a) providing an isolated or recombinant polypeptide comprising a sequence having at least 95% sequence identity to SEQ ID NO:2, wherein the polypeptide is capable inhibiting apoptosis in a plant cell, and, (a) contacting the polypeptide with the plant in an amount sufficient to inhibit apoptosis in the plant, thereby generating a plant that is biotic insult resistant. The invention provides a method for generating an abiotic or biotic insult-resistant plant comprising the following steps: (a) providing an isolated or recombinant nucleic acid comprising a sequence having at least 95% sequence identity to SEQ ID NO:1, wherein the nucleic acid encodes polypeptide capable of inhibiting apoptosis in a plant cell, and, (b) contacting the nucleic acid with the plant and expressing the nucleic acid to produce an amount of polypeptide sufficient to inhibit apoptosis in the plant. In alternative aspects of these methods, the biotic insult is induced by a plant pathogen, such as a virus, a fungus, a bacteria or a nemotode. In alternative aspects of these methods, the abiotic insult is induced by high moisture, low moisture, salinity, nutrient deficiency, air pollution, high temperature, low temperature, soil toxicity, herbicides or insecticides.

The details of one or more embodiments of the invention are set forth in the accompanying drawings and the description below. Other features, objects, and advantages of the invention will be apparent from the description and drawings, and from the claims.

All publications, patents, patent applications, GenBank™ sequences and ATCC deposits, cited herein are hereby expressly incorporated by reference for all purposes.

DESCRIPTION OF DRAWINGS

(FIG. 2B) BmIAP-BIR, (FIG. 2C) BmIAP-RING; and, (FIG. 2E) AcIAP; in 2B, 2C and 2E the apoptotic body formation (without occlusion body formation) are indicated by arrowheads. FIG. 2F depicts control uninfected SF-21 cells. Full details in Example 1, below.

In FIG. 3C recombinant BmIAP was added to cytosolic extracts from HEK293 cells concurrently with the addition of cytochrome-c and dATP. Full details in Example 1, below.

FIG. 4A: Recombinant active caspase-9 was incubated with Ac-LEHD-AFC substrate in the presence or absence of various concentration of recombinant purified BmIAP or SfIAP. FIG. 4B: Recombinant caspase-3 was incubated with Ac-DEVD-AFC substrate in the presence or absence of GST-XIAP, GST-BmIAP or 0.5 uM GST-SfIAP. FIG. 4C: Recombinant caspase-7 was incubated with Ac-DEVD-AFC substrate in the presence or absence of GST-XIAP, GST-BmIAP or GST-SfIAP. Full details in Example 1, below.

Like reference symbols in the various drawings indicate like elements.

DETAILED DESCRIPTION

Figure 1:
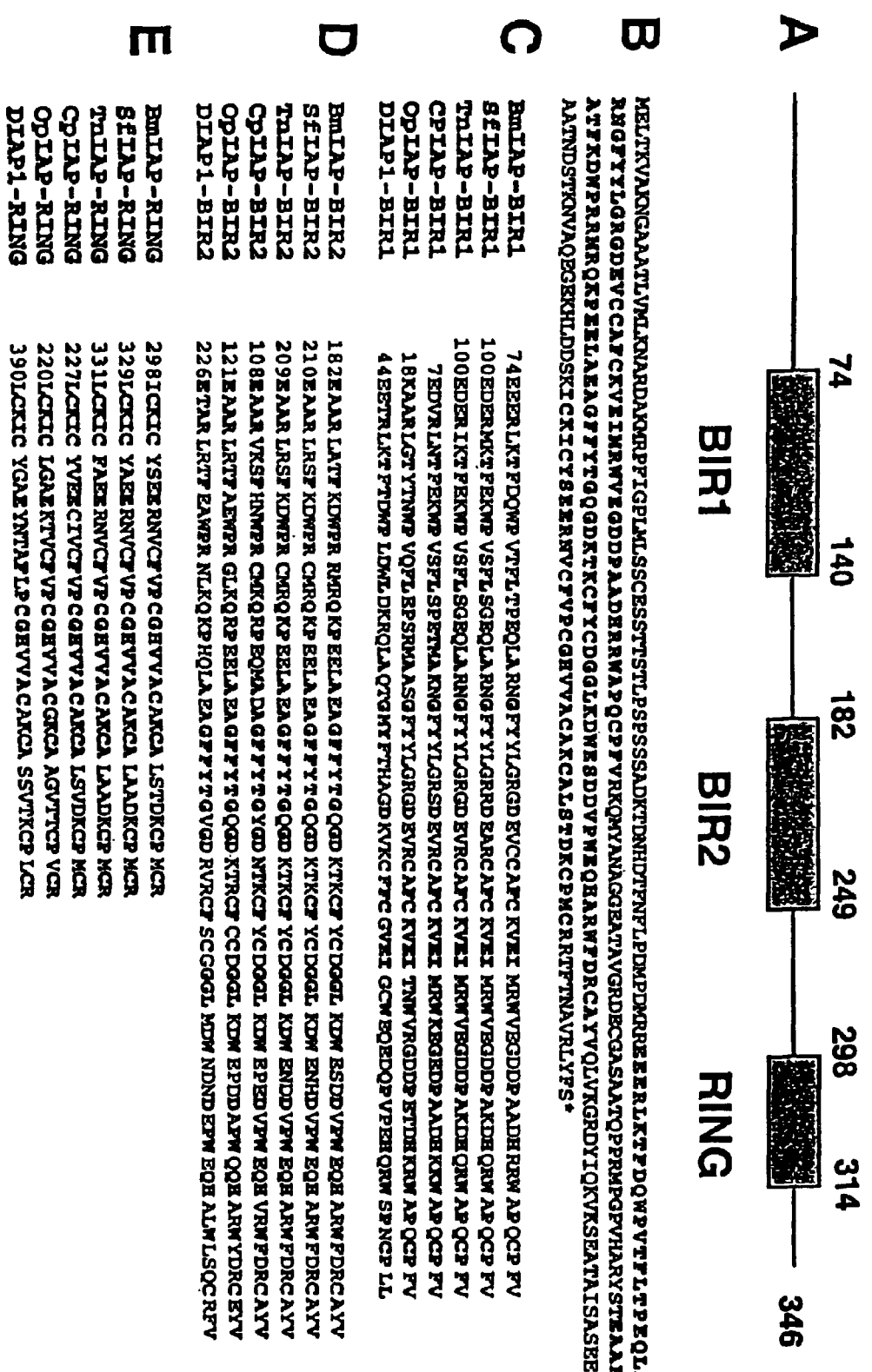
FIG. 1A is a schematic showing the location of the BIR domains (BIR1, residues 74 to 140; BIR2, residues 182 to 249; of SEQ ID NO:2, as set forth in Example 1, below) and the RING domain (residues 298 to 314; of SEQ ID NO:2) of BmIAP.
FIG. 1B (SEQ ID NO:2) is the full length amino acid sequence of BmIAP (also set forth in Example 1, below, as SEQ ID NO:2). Sequence alignments of the BIR1 (FIG. 1C) (SEQ ID NOS: 8-13, respectively in order of appearance), BIR2 (FIG. 1D) (SEQ ID NOS:14-19, respectively in order of appearance) and RING (FIG. 1E) (SEQ ID NOS 20-25, respectively in order of appearance) domains of BmIAP with the corresponding domains of other IAP family members are shown. Bold text indicates identical amino acid. See Example 1, below.

The invention provides polypeptides that are "inhibitors of apoptosis protein (IAP) family members," including the exemplary BmIAP (SEQ ID NO:2), and nucleic acids encoding them (e.g., SEQ ID NO:1), and methods for making and using these compositions. BmIAP was initially derived from lepidopteran *Bombyx mori* BmN cells.

The polypeptides and nucleic acids of the invention can be used for inhibiting caspases, including insect, plant and mammalian caspases, such as human caspase 9, and "programmed cell death," or apoptosis. The polypeptides of the invention have some amino acid sequence similarity with SfIAP (see, e.g., Huang (2000) Proc. Natl. Acad. Sci. USA 97:1427-1432), TnIAP and baculoviral CpIAP. As discussed herein, structure-function analysis of BmIAP (SEQ ID NO:2) reveals identical domain requirements (e.g. BIR plus RING, see FIG. 1A) for suppression of apoptosis in both insect and mammalian cells, and similar caspase selectivity (e.g. caspase-9) compared to the previously characterized lepidopteran and baculovirus IAPs. These results strongly support the idea that lepidopteran IAPs are evolutionary conserved in both sequence and function. Accordingly, the compositions and methods of the invention are used to manipulate apoptotic ("cell death") mechanisms in a variety of cell types, including insect, plant and mammalian, such as human, cells, and organisms.

*Drosophila* and mammalian IAPs have been shown to play important roles in the development of these organisms (see, e.g., Hay (1995) Cell 83:1253-1262; Holcik (2000) Proc. Natl. Acad. Sci. USA 97(5), 2286-2290). By analogy, the exemplary BmIAP (SEQ ID NO:2) is also a critical player in silkworm development. Accordingly, the compositions and methods of the invention can be used to manipulate apoptosis during the development of the silkworm. Lepidopteran and coleopteran cells, e.g., *Bombyx mori* cells and *Spodoptera frugiperda* cells, are commonly used in conjunction with expression vectors (recombinant viruses) to express large quantities of exogenous polypeptides (see, e.g., Juntunen (1999) Biochem J. 344 Pt 2:297-303); the compositions and methods of the invention can be used to manipulate these expression systems. Thus, the compositions and methods of the invention will have a significant impact on sericulture and biotechnology industries, particularly those related to the silkworm.

Example 1, below, describes the isolation and characterization of a novel group of "Inhibitor of Apoptosis Proteins (IAP)," designated BmIAP. An exemplary polypeptide of this BmIAP group has a sequence as set forth in SEQ ID NO:2; an exemplary nucleic acid encodes it having a sequence as set forth in SEQ ID NO:1. The exemplary IAP polypeptide and nucleic acid of the invention were initially derived from *Bombyx mori* BmN cells. BmIAP (SEQ ID NO:2) contains two baculoviral IAP repeat (BIR) domains followed by a RING domain (the BIR domain contains a highly conserved arrangement of Cys/His residues forming a stable fold that chelates zinc and the RING finger is a common zinc-binding motif that also exists in other cellular proteins), see FIG. 1A. BmIAP shares some common structural and functional properties with lepidopteran IAPs, SfIAP and TnIAP, and with two baculoviral IAPs, CpIAP and CpIAP, suggesting evolutionary conservation.

The polypeptides of the invention, "BmIAP," block programmed cell death (apoptosis) in *Spodoptera frugiperda* Sf-21 cells induced by p35 (apoptosis inhibiting)-deficient *Autographa californica* nucleopolyhedrovirus (AcMNPV). BmIAP's anti-apoptotic function requires both the BIR domains and RING domain. In mammalian cells, BmIAP inhibits Bax-induced but not Fas-induced apoptosis. The data discussed below demonstrates that BmIAP can inhibit mammalian caspase-9 (an initiator caspase in the mitochondria/cytochrome-c pathway), and may be a specific inhibitor of caspase 9, but not the downstream effector proteases, caspase-3 and caspase-7. While the invention is not limited by any particular mechanism of action, these data support the role of the polypeptides of the invention in suppressing apoptosis as involving inhibition of an upstream initiator caspase (e.g., mammalian caspase-9) in the conserved mitochondria/cytochrome-c pathway. Inhibition of such caspases effectively also inhibit apoptosis.

DEFINITIONS

Unless defined otherwise, all technical and scientific terms used herein have the meaning commonly understood by a person skilled in the art to which this invention belongs. As used herein, the following terms have the meanings ascribed to them unless specified otherwise.

The term "antibody" or "Ab" includes both intact antibodies having at least two heavy (H) chains and two light (L) chains inter-connected by disulfide bonds and antigen binding fragments thereof, or equivalents thereof, either isolated from natural sources, recombinantly generated or partially or entirely synthetic. Examples of antigen binding fragments include, e.g., Fab fragments, F(ab')2 fragments, Fd fragments, dAb fragments, isolated complementarity determining regions (CDR), single chain antibodies, chimeric antibodies, humanized antibodies, human antibodies made in non-human animals (e.g., transgenic mice) or any form of antigen binding fragment.

The terms "array" or "microarray" or "DNA array" or "nucleic acid array" or "biochip" as used herein is a plurality of target elements, each target element comprising a defined amount of one or more nucleic acid molecules, including the nucleic acids of the invention, immobilized a solid surface for hybridization to sample nucleic acids, as described in detail, below. The nucleic acids of the invention can be incorporated into any form of microarray, as described, e.g., in U.S. Pat. Nos. 6,045,996; 6,022,963; 6,013,440; 5,959,098; 5,856,174; 5,770,456; 5,556,752; 5,143,854.

A "biotic insult", as used herein, refers to plant challenge caused by viable or biologic agents (biotic agents), such as insects, fungi, bacteria, viruses, nematodes, viroids, mycoplasmas, and the like.

An "abiotic insult", as used herein, refers to plant challenge by a non-viable or non-living agent (abiotic agent). Abiotic agents that can cause an abiotic insult include, for example, environmental factors such as low moisture (drought), high moisture (flooding), nutrient deficiency, radiation levels, air pollution (ozone, acid rain, sulfur dioxide, etc.), temperature (hot and cold extremes), and soil toxicity, as well as herbicide damage, pesticide damage, or other agricultural practices (e.g., over-fertilization, improper use of chemical sprays, etc.).

The term "expression cassette" refers to any recombinant expression system for the purpose of expressing a nucleic acid sequence of the invention in vitro or in vivo, constitutively or inducibly, in any cell, including, in addition to insect and plant cells, prokaryotic, yeast, fungal or mammalian cells. The term includes linear or circular expression systems. The term includes all vectors. The cassettes can remain episomal or integrate into the host cell genome. The expression cassettes can have the ability to self-replicate or not, i.e., drive only transient expression in a cell. The term includes recombinant expression cassettes that contain only the minimum elements needed for transcription of the recombinant nucleic acid.

The term "heterologous" when used with reference to a nucleic acid, indicates that the nucleic acid is in a cell or plant where it is not normally found in nature; or, comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature; e.g., a promoter sequence operably linked to a nucleic of the invention. As another example, the invention provides recombinant constructs (expression cassettes, vectors, viruses, and the like) comprising various combinations of promoters and sequences of the invention.

As used herein, "isolated," when referring to a molecule or composition, such as, e.g., a nucleic acid or polypeptide of the invention, means that the molecule or composition is separated from at least one other compound, such as a protein, DNA, RNA, or other contaminants with which it is associated in vivo or in its naturally occurring state. Thus, a nucleic acid sequence is considered isolated when it has been isolated from any other component with which it is naturally associated. An isolated composition can, however, also be substantially pure. An isolated composition can be in a homogeneous state. It can be in a dry or an aqueous solution. Purity and homogeneity can be determined, e.g., using analytical chemistry techniques such as, e.g., polyacrylamide gel electrophoresis (SDS-PAGE) or high performance liquid chromatography (HPLC).

The term "nucleic acid" or "nucleic acid sequence" refers to a deoxy-ribonucleotide or ribonucleotide oligonucleotide, including single- or double-stranded forms, and coding or non-coding (e.g., "antisense") forms. The term encompasses nucleic acids containing known analogues of natural nucleotides. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). The term nucleic acid is used interchangeably with gene, DNA, RNA, cDNA, mRNA, oligonucleotide primer, probe and amplification product.

As used herein the terms "polypeptide," "protein," and "peptide" are used interchangeably and include compositions of the invention that also include "analogs," or "conservative variants" and "mimetics" (e.g., "peptidomimetics") with structures and activity that substantially correspond to the polypeptides of the invention, including the exemplary sequence as set forth in SEQ ID NO:2. Thus, the terms "conservative variant" or "analog" or "mimetic" also refer to a polypeptide or peptide which has a modified amino acid sequence, such that the change(s) do not substantially alter the polypeptide's (the conservative variant's) structure and/or activity (e.g., ability to inhibit caspase 9, to inhibit apoptosis), as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W); (see also, e.g., Creighton (1984) Proteins, W.H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides of the invention (e.g., ability to inhibit apoptosis, antigenicity, etc.). The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetics' structure and/or activity. As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, N.Y.). A polypeptide can also be characterized as a mimetic by containing all or some non-natural residues in place of naturally occurring amino acid residues; non-natural residues are well described in the scientific and patent literature.

As used herein, a "pathogen" refers to any agent that causes a disease or disease state in an animal or plant, including, but not limited to viruses, fungi, bacterium, nematodes, and other related microorganisms.

The term "plant" includes whole plants, plant parts (e.g., leaves, stems, flowers, roots, etc.), plant protoplasts, seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. Plantlets are also included within the meaning of "plant". Suitable plants for use in the invention include any plants amenable to transformation techniques, including both monocotyledonous and dicotyledonous plants. Examples of monocotyledonous plants include, but are not limited to, asparagus, field and sweet corn, barley, wheat, rice, sorghum, onion, pearl millet, rye and oat, and ornamentals. Examples of dicotyledonous plants include, but are not limited to, tomato, potato, arabidopsis, tobacco, cotton, rapeseed, field beans, soybeans, peppers, lettuce, peas, alfalfa, clover, cole crops or *Brassica* (e.g., cabbage, broccoli, cauliflower, brussel sprouts), radish, carrot, beets, eggplant, spinach, cucumber, squash, melons, cantaloupe, sunflowers and various ornamentals. The term "plant cell", as used herein, refers to protoplasts, gamete producing cells, and cells that are capable of regenerating into whole plants. Accordingly, a seed comprising multiple plant cells capable of regenerating into a whole plant is included in the definition of "plant cell". As used herein, "plant tissue" includes differentiated and undifferentiated tissues of a plant, including but not limited to roots, stems, shoots, leaves, pollen, seeds, tumor tissue and various forms of cells and culture such as single cells, protoplast, embryos, and callus tissue.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

As used herein, the term "promoter" includes all sequences capable of driving transcription of a coding sequence in a cell, including an insect cell, a plant cell, a mammalian cell, and the like. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

The term percent "sequence identity," in the context of two or more nucleic acids or polypeptide sequences refers to two or more sequences or subsequences that are the same or have a specified percentage of nucleotides (or amino acid residues) that are the same, when compared and aligned for maximum correspondence over a comparison window, as measured using one of the following sequence comparison algorithms or by manual alignment and visual inspection. This definition also refers to the complement (antisense strand) of a sequence. For example, in alternative embodiments, nucleic acids within the scope of the invention include those with an amino acid sequence identity that is at least about 95%, at least about 96%, at least about 97%, at least about 98%, at least about 99% of the exemplary sequences set forth in SEQ ID NO:2 Two sequences with these levels of identity are "substantially identical" and within the scope of the invention. Thus, if a nucleic acid sequence has the requisite sequence identity to SEQ ID NO:1, or a subsequence thereof, it also is a polynucleotide sequence within the scope of the invention. If an amino acid sequence has the requisite sequence identity to SEQ ID NO:2, or a subsequence thereof, it also is a polypeptide within the scope of the invention. In one aspect, the percent identity exists over a region of the sequence that is at least about 25 nucleotides or amino acid residues in length, or, over a region that is at least about 50 to 100 nucleotides or amino acids in length. Parameters (including, e.g., window sizes, gap penalties and the like) to be used in calculating "percent sequence identities" between two nucleic acids or polypeptides to identify and determine whether one is within the scope of the invention are described in detail, below.

Polypeptides and Peptides

The invention provides an isolated or recombinant polypeptide comprising a sequence having at least 95% sequence identity to SEQ ID NO:2. One exemplary polypeptide comprises the sequence as set forth in SEQ ID NO:2, and fragments (e.g., antigenic fragments) thereof (as noted above, the term polypeptide includes peptides and peptidomimetics, etc.). Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art.

Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer). The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234. Modified peptides of the invention can be further produced by chemical modification methods, see, e.g., Belousov (1997) Nucleic Acids Res. 25:3440-3444; Frenkel (1995) Free Radic. Biol. Med. 19:373-380; Blommers (1994) Biochemistry 33:7886-7896.

The invention provides a fusion protein comprising a polypeptide of the invention, e.g., a sequence having at least 95% sequence identity to SEQ ID NO:2, and a second domain. Thus, peptides and polypeptides of the invention are synthesized and expressed as chimeric or "fusion" proteins with one or more additional domains linked thereto for, e.g., to more readily isolate or identify a recombinantly synthesized peptide, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wass.). The inclusion of a cleavable linker sequences such as Factor Xa or enterokinase (Invitrogen, San Diego Calif.) between the purification domain and GCA-associated peptide or polypeptide can be useful to facilitate purification. For example, an expression vector can include an epitope-encoding nucleic acid sequence linked to six histidine residues followed by a thioredoxin and an enterokinase cleavage site (see, e.g., Williams (1995) Biochemistry 34:1787-1797; Dobeli (1998) Protein Expr. Purif. 12:404-14). The histidine residues facilitate detection and purification while the enterokinase cleavage site provides a means for purifying the epitope from the remainder of the fusion protein.

Nucleic Acids, Expression Vectors and Transformed Cells

The invention provides an isolated or recombinant nucleic acid comprising a nucleic acid sequence having at least 95% sequence identity to SEQ ID NO:1, and expression cassettes (e.g., vectors), cells and transgenic animals comprising the nucleic acids of the invention. As the genes and vectors of the invention can be made and expressed in vitro or in vivo, the invention provides for a variety of means of making and expressing these genes and vectors. One of skill will recognize that desired phenotypes associated with altered gene activity can be obtained by modulating the expression or activity of the genes and nucleic acids (e.g., promoters) within the expression cassettes (e.g., vectors) of the invention. Any of the known methods described for increasing or decreasing expression or activity can be used for this invention. The invention can be practiced in conjunction with any method or protocol known in the art, which are well described in the scientific and patent literature.

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to insect and bacterial cells, e.g., mammalian, yeast or plant cell expression systems.

Alternatively, these nucleic acids can be synthesized in vitro by well-known chemical synthesis techniques, as described in, e.g., Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., generating mutations in sequences, subcloning, labeling probes, sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

The invention provides nucleic acids of the invention "operably linked" to a transcriptional regulatory sequence. "Operably linked" refers to a functional relationship between two or more nucleic acid (e.g., DNA) segments. Typically, it refers to the functional relationship of a transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. For example, in one embodiment, a promoter is operably linked to a nucleic acid sequence of the invention, as exemplified by SEQ ID NO:1.

The invention further provides cis-acting transcriptional regulatory sequences, which, in vivo, are operably linked to the coding sequence for the exemplary polypeptide of the invention, SEQ ID NO:2, including promoters, comprising the genomic sequences 5' (upstream) of a transcriptional start site (see SEQ ID NO:1) and intronic sequences. The promoters of the invention contain cis-acting transcriptional regulatory elements involved in message expression. These promoter sequences may be readily obtained using routine molecular biological techniques. For example, additional genomic (and promoter) sequences may be obtained by screening Bombyx mori genomic libraries using nucleic acids of the invention. For example, genomic sequence can be readily identified by "chromosome walking" techniques, as described by, e.g., Hauser (1998) Plant J 16:117-125; Min (1998) Biotechniques 24:398-400. Other useful methods for further characterization of promoter sequences include those general methods described by, e.g., Pang (1997) Biotechniques 22:1046-1048; Gobinda (1993) PCR Meth. Applic. 2:318; Triglia (1988) Nucleic Acids Res. 16:8186; Lagerstrom (1991) PCR Methods Applic. 1:111; Parker (1991) Nucleic Acids Res. 19:3055. As is apparent to one of ordinary skill in the art, these techniques can also be applied to identify, characterize and isolate any genomic or cis-acting regulatory sequences corresponding to or associated with the nucleic acid and polypeptide sequences of the invention.

The invention provides oligonucleotide primers that can amplify all or any specific region within a nucleic acid sequence of the invention, particularly, the exemplary SEQ ID NO:1. The nucleic acids of the invention can also be mutated, detected, generated or measured quantitatively using amplification techniques. Using the nucleic acid sequences of the invention (e.g., as in the exemplary SEQ ID NO:1), the skilled artisan can select and design suitable oligonucleotide amplification primers. Amplification methods are also known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y.); ligase chain reaction (LCR) (see, e.g., Barringer (1990) Gene 89:117); transcription amplification (see, e.g., Kwoh (1989) Proc. Natl. Acad. Sci. USA, 86:1173); and, self-sustained sequence replication (see, e.g., Guatelli (1990) Proc. Natl. Acad. Sci. USA, 87:1874); Q Beta replicase amplification (see, e.g., Smith (1997) J. Clin. Microbiol. 35:1477-1491; Burg (1996) Mol. Cell. Probes 10:257-271) and other RNA polymerase mediated techniques (e.g., NASBA, Cangene, Mississauga, Ontario).

Expression vectors capable of expressing the nucleic acids and polypeptides of the invention in animal cells, including insect and mammalian cells, are well known in the art. Vectors which may be employed include recombinantly modified enveloped or non-enveloped DNA and RNA viruses, e.g., from baculoviridiae, parvoviridiae, picornoviridiae, herpesveridiae, poxviridae, adenoviridiae, picornnaviridiae or alphaviridae. Insect cell expression systems commonly use recombinant variations of baculoviruses and other nucleopolyhedrovirus, e.g., Bombyx mori nucleopolyhedrovirus vectors (see, e.g., Choi (2000) Arch. Virol. 145:171-177). For example, Lepidopteran and Coleopteran cells are used to replicate baculoviruses to promote expression of foreign genes carried by baculoviruses, e.g., Spodoptera frugiperda cells are infected with recombinant Autographa californica nuclear polyhedrosis viruses (AcNPV) carrying a heterologous, e.g., a human, coding sequence (see, e.g., Lee (2000) J. Virol. 74:11873-11880; Wu (2000) J. Biotechnol. 80:75-83). See, e.g., U.S. Pat. No. 6,143,565, describing use of the polydnavirus of the parasitic wasp Glyptapanteles indiensis to stably integrate nucleic acid into the genome of Lepidopteran and Coleopteran insect cell lines. See also, U.S. Pat. Nos. 6,130,074; 5,858,353; 5,004,687.

Mammalian expression vectors can be derived from adenoviral, adeno-associated viral or retroviral genomes. Retroviral vectors can include those based upon murine leukemia virus (see, e.g., U.S. Pat. No. 6,132,731), gibbon ape leukemia virus (see, e.g., U.S. Pat. No. 6,033,905), simian immuno-deficiency virus, human immuno-deficiency virus (see, e.g., U.S. Pat. No. 5,985,641), and combinations thereof. Describing adenovirus vectors, see, e.g., U.S. Pat. Nos. 6,140,087; 6,136,594; 6,133,028; 6,120,764. See, e.g., Okada (1996) Gene Ther. 3:957-964; Muzyczka (1994) J. Clin. Invst. 94:1351; U.S. Pat. Nos. 6,156,303; 6,143,548 5,952,221, describing AAV vectors. See also U.S. Pat. Nos. 6,004,799; 5,833,993.

Expression vectors capable of expressing proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

The invention provides a transformed cell comprising a nucleic acid of the invention. The cells can be mammalian (such as human), insect (such as *Spodoptera frugiperda, Spodoptera exigua, Spodoptera littoralis, Spodoptera litura, Pseudaletia separata, Trichoplusia ni, Plutella xylostella, Bombyx mori, Lymantria dispar, Heliothis virescens, Autographica californica* and other insect, particularly lepidopteran and coleopteran, cell lines), plant, bacterial, yeast, and the like. Techniques for transforming and culturing cells are well described in the scientific and patent literature; see, e.g., Weiss (1995) Methods Mol. Biol. 39:79-95, describing insect cell culture in serum-free media; Tom (1995) Methods Mol. Biol. 39:203-224; Kulakosky (1998) Glycobiology 8:741-745; Altmann (1999) Glycoconj. J. 16:109-123; Yanase (1998) Acta Virol. 42:293-298; U.S. Pat. Nos. 6,153,409; 6,143,565; 6,103,526.

Transgenic Non-human Animals

The invention also provides transgenic animals, including mammals and insects. Insects stably expressing the nucleic acids of the invention can be used for, e.g., experiments studies on apoptosis, screening for modulators of caspases and apoptosis, manipulation of insect life cycles, such as *Bombyx mori* and its use in silk production. The nucleic acids of the invention can be expressed in a variety of insect larvae, e.g., *Bombyx mori* (see, e.g., Maeda (1985) Nature 315: 592-594), *Trichoplusia ni*, the cabbage looper larvae (Medin (1990) Proc. Nat. Acad. Sci. USA 87: 2760-2764) and *Manduca sexta*, the tobacco hornworm (U.S. Pat. No. 5,471,858). See, e.g., Keshan (2000) J. Insect Physiol. 46:1061-1068; U.S. Pat. No. 5,118,616.

The invention also provides transgenic non-human mammals, e.g., goats, rats and mice, comprising the chimeric nucleic acids of the invention. These animals can be used, e.g., as in vivo models to study apoptosis, or, as models to screen for modulators of caspase enzyme activity in vivo. Transgenic non-human animals can be designed and generated using any method known in the art; see, e.g., U.S. Pat. Nos. 6,156,952; 6,118,044; 6,111,166; 6,107,541; 5,959,171; 5,922,854; 5,892,070; 5,880,327; 5,891,698; 5,639,940; 5,573,933, describing making and using transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats.

Transgenic Plants

The invention also provides transgenic plants, including seeds, expressing the nucleic acids and polypeptide of the invention. Nucleic acids may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Alternatively, transformed plant cells can be generated by fusion of the recipient cells with bacterial protoplasts containing DNA, use of DEAE dextran, polyethylene glycol precipitation, as described, e.g., in Paszkowski (1984) EMBO J. 3:2717-2722. DNA construct can be introduced directly into the genomic DNA of the plant cell using electroporation, as described, e.g., in Fromm (1985) Proc. Natl. Acad. Sci. USA 82:5824, or by microinjection of plant cell protoplasts, as described, e.g., Schnorf (1991) Transgenic Res. 1:23-30.

Nucleic acids can be introduced directly to plant tissue using ballistic methods, such as DNA particle bombardment. Microprojectile bombardment to deliver DNA into plant cells is an alternative means of transformation for the numerous species considered recalcitrant to *Agrobacterium*- or protoplast-mediated transformation methods. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

DNA can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) Science 233:496-498; Fraley (1983) Proc. Natl. Acad. Sci. USA 80:4803 (1983); *Gene Transfer to Plants*, Potrykus, ed. (Springer-Verlag, Berlin 1995).

Alignment Analysis of Sequences

The nucleic acid sequences of the invention include genes and gene products identified and characterized by analysis using the exemplary nucleic acid and protein sequences of the invention, including SEQ ID NO:1 and SEQ ID NO:2. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used unless alternative parameters are designated herein. The sequence comparison algorithm then calculates the percent sequence identity for the test sequence(s) relative to the reference sequence, based on the designated or default program parameters. A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned.

Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (CLUSTAL, GAP, BESTFIT, FASTA, and TFASTA in the Wisconsin Genetics Software Package, Genetics Computer Group, 575 Science Dr., Madison, Wis.), or by manual alignment and visual inspection.

In one aspect, a CLUSTAL algorithm, such as the CLUSTAL W program, is used to determine if a nucleic acid or polypeptide sequence is within the scope of the invention; see, e.g., Thompson (1994) Nuc. Acids Res. 22:4673-4680; Higgins (1996) Methods Enzymol 266:383-402. Variations can also be used, such as CLUSTAL X, see Jeanmougin (1998) Trends Biochem Sci 23:403-405; Thompson (1997) Nucleic Acids Res 25:4876-4882. CLUSTAL W program, described by Thompson (1994) supra, in the methods of the invention used with the following parameters: K tuple (word) size: 1, window size: 5, scoring method: percentage, number of top diagonals: 5, gap penalty: 3.

Another algorithm is PILEUP, which can be used to determine whether a polypeptide or nucleic acid has sufficient sequence identity to SEQ ID NO:1 or SEQ ID NO:2 to be with the scope of the invention. This program creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The following parameters are used with PILEUP in the methods of the invention: default gap weight (3.00), default gap length weight (0.10), and weighted end gaps.

Another example of an algorithm that is suitable for determining percent sequence identity (i.e., substantial similarity or identity) in this invention is the BLAST algorithm, which is described in Altschul (1990) J. Mol. Biol. 215:403-410. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a nucleic acid sequence is within the scope of the invention, the BLASTN program (for nucleotide sequences) is used incorporating as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see, e.g., Henikoff (1989) Proc. Natl. Acad. Sci. USA 89:10915).

Antibodies

The invention provides antibodies that specifically bind to the polypeptides of the invention, e.g., the exemplary SEQ ID NO:2. These antibodies can be used, e.g., to isolate the polypeptides of the invention, to identify the presence of polypeptides that are associated with apoptosis, and the like. To generate antibodies, polypeptides or peptides (antigenic fragments of SEQ ID NO:2) can be conjugated to another molecule or can be administered with an adjuvant. The coding sequence can be part of an expression cassette or vector capable of expressing the immunogen in vivo (see, e.g., Katsumi (1994) Hum. Gene Ther. 5:1335-9). Methods of producing polyclonal and monoclonal antibodies are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif.; Goding, MONOCLONAL ANTIBODIES: PRINCIPLES AND PRACTICE (2d ed.) Academic Press, New York, N.Y. (1986); Harlow (1988) ANTIBODIES, A LABORATORY MANUAL, Cold Spring Harbor Publications, New York.

Antibodies also can be generated in vitro, e.g., using recombinant antibody binding site expressing phage display libraries, in addition to the traditional in vivo methods using animals. See, e.g. Huse (1989) Science 246:1275; Ward (1989) Nature 341:544; Hoogenboom (1997) Trends Biotechnol. 15:62-70; Katz (1997) Annu. Rev. Biophys. Biomol. Struct. 26:27-45. Human antibodies can be generated in mice engineered to produce only human antibodies, as described by, e.g., U.S. Pat. Nos. 5,877,397; 5,874,299; 5,789,650; and 5,939,598. B-cells from these mice can be immortalized using standard techniques (e.g., by fusing with an immortalizing cell line such as a myeloma or by manipulating such B-cells by other techniques to perpetuate a cell line) to produce a monoclonal human antibody-producing cell. See, e.g., U.S. Pat. Nos. 5,916,771; 5,985,615.

Measuring Markers of Apoptosis in a Cell

The invention provides a method for identifying an agent that can modulate the activity of a polypeptide of the invention (e.g., a polypeptide having a sequence at least 95% sequence identity to SEQ ID NO:2) that is capable inhibiting apoptosis in a cell. The method comprises contacting a cell expressing the polypeptide recombinantly in the presence and absence of a test agent before, during or after inducing apoptosis in the cell; and, measuring the amount or degree of the polypeptide's activity in the cell in the presence and absence of the test agent, wherein an increase or decrease in the amount or degree of apoptosis in the cell in the presence of the test agent identifies the test agent as a modulator of the polypeptide's activity.

The degree of the polypeptide's activity in the cell can be determined by measuring the amount or degree of apoptosis in the cell; the amount or degree of caspase protease activity in the cell; the amount or degree of DNA fragmentation in the cell; the amount or degree of cleavage of substrates of caspases in the cell; or by measuring the amount or degree of any surrogate marker of apoptosis in the cell; methods for making these measurements are well known in the art, and the invention incorporates all such methods and variations thereof. For example, see Methods in Enzymology (2000) volume 322, edited by John C. Reed, Academic Press, e.g., chapters on pages 3, 15, 41, describing assays to measure apoptosis and surrogate markers of apoptosis and enzymes with activity related to levels of apoptosis, e.g., assays to determine DNA fragmentation, caspase assays, measuring annexin V (see, e.g., Zhang (1997) Biotechniques 23:525-531), and the like. See, e.g., van Engeland (1996) Cytometry 24:131-139; Gorczyca (1998) Methods Mol. Biol. 91:217-238. See also, e.g., U.S. Pat. Nos. 6,165,737; 6,165,732; 6,160,095; 6,143,522; 6,087,384; 6,077,684; 6,060,238; 6,054,436; 5,985,829; 5,976,786; 5,952,189.

EXAMPLES

The following example is offered to illustrate, but not to limit the claimed invention.

Example 1

Cloning, Recombinant Expression and Characterization of BmIAP

The following example describes the initial cloning of the BmIAP of the invention, recombinant expression of BmIAP nucleic acids and polypeptides and characterization of the BmIAP of the invention.

Cloning of BmIAP: mRNA was isolated from BmN cells by using a kit from Qiagen, Inc. (Valencia, Calif.). Degenerate primers were used; they were designed according to the consensus amino acid sequences between baculoviral IAPs and Drosophila IAPs, having the sequence 5'-GC(A/C/G/T)GA(A/C/G/T)GC(A/C/G/T)GG(A/C/G/T) TT(T/C)TT(T/C)TA-3' (SEQ ID NO:3) and 5'-AC(A/C/G/T)AC(A/G)TG(A/C/G/T)CC (A/G)CA(A/C/G/T)GG-3' (SEQ ID NO:4). Reverse transcription-PCR was performed for 35 cycles by using 94° C. for 45 sec, 46° C. for 1 min and 72° C. for 1 min. Amplified fragments were blunt-end-cloned into HincII site of pTZ-19 and then sequenced. To obtain full-length BmIAP cDNAs, 5' RACE and 3' RACE were performed by using commercial kits (GIBCO/BRL; Takara) and 5'-CTGTTC-CCACGGAACGTC-3' (SEQ ID NO:5) and 5'-GCCAC-CAATGATTCGAC-3' (SEQ ID NO:6) as internal PCR primers.

Plasmid construction: A cDNA fragment encompassing the complete ORF of BmIAP was PCR-amplified and subcloned into the EcoRI-XhoI sites in pcDNA3-myc and pGEX4T-1. Plasmids encoding fragments of BmIAP, including BIR1+2 (amino acid residue 1-292) (SEQ ID NO:2) and RING (residue 293-346) (SEQ ID NO:2), were amplified by PCR by using primers containing either start or stop codons as appropriate and subcloned into pTZ-19 and pcDNA3-myc plasmids.

Protein expression and purification: pGEX4T-1-BmIAP plasmid was introduced into E. coli strain BL21 (DE3) containing the plasmid pT-Trx. Glutathione S-transferase (GST) fusion proteins were obtained by induction with 0.05 mM isopropyl β-thiogalactoside at 25° C. for 8 hr and then purified using glutathione-Sepharose (see, e.g., Huang (2000) Proc. Natl. Acad. Sci. USA 97:1427-1432). The catalytic domains of caspase-3, caspase-7 and caspase-9 were expressed, purified by Ni-chelation affinity-chromatography, and quantified as described by Stennicke (1997) J. Biol. Chem. 272:25719-25723; Stennicke (1998) J. Biol. Chem 273:27084-27090; Stennicke (1999) J. Biol. Chem. 274: 8359-8362.

Cell extracts and Caspase assays: Cytosolic extracts were prepared by using human embryonic kidney (HEK) 293 cells (see, e.g., Deveraux (1997) Nature 388:300-303). For initiating caspase activation, 1 uM horse heart cytochrome-c (Sigma) and 1 mM dATP was added to extracts, as described by Deveraux (1998) Embo J. 17:2215-2223). Caspase activity was assayed by release of 7-amino-4-trifluoromethyl-coumarin (AFC) from Ac-DEVD-AFC or Ac-LEHD-AFC (Calbiochem), using a spectrofluorimeter as described by Stennicke (1997) supra; Quan (1995) J. Biol. Chem. 270: 10377-10379.

Cell culture, Transfection an dApoptosis Assays: Insect Sf-21 cells were maintained at 27° C. in Excell 401 medium (JRH Biosciences, Lenexa, Kans.) supplemented with 2.5% FBS. vP35del, Autographa califonica nuclear polyhedrosis virus (AcMNPV) containing a deletion in the apoptosis suppressor "p35" gene (35-kilodalton protein gene) (see, e.g., Lerch (1993) Nucleic Acids Res. 21:1753-1760) was propagated in TN-386 cells (see, e.g., Clem (1991) Science 254: 1388-1390). Plasmids encoding full-length or deletion mutants of BmIAP (ug) were co-transfected with 1 ug vP35del viral DNA into Sf-21 cells by using Lipofectin™ from GIBCO/BRL. Occlusion body formation was observed under light-microscopy 3 days post-transfection. HEK293 cells were maintained in DMEM (Irvine Scientific) supplemented with 10% FBS, 1 mM L-glutamine, and antibiotics. 293 cells ($10^6$) were cotransfected by using Superfect™ (Qiagen) with 0.1 ug of green fluorescence protein (GFP) marker plasmid pEGFP (CLONTECH), 0.25 ug of either pcDNA3-Bax or pcDNA3-Fas and 1.5 ug of pcDNA3-myc-BmIAP. Both floating and adherent cells were recovered 24 to 36 hour post-transfection and pooled, and the percentage of GFP-positive cells with nuclear apoptotic morphology was determined by staining with 0.1 ug/ml 4'-6-diamidino-2-phenylindole (DAPI) (mean+/−S.D.; n=3) as described by Takhashi (1998) J. Biol. Chem. 273:7787-7790.

The full-length BmIAP cDNA (SEQ ID NO:1) and the BmIAP polypeptide amino acid sequence (SEQ ID NO:1) are:

BmIAP cDNA nucleotide sequence:
(SEQ ID NO: 1)

```
   1 CATTATTAAA CTCACTTCAC TTCGGTAGTG TGAATGTTAA CGTGAAACTC CGCGCTCTTC
  61 TTTAGTTGCT ACTCGGTTCT GTCTGGCTGC GTTGACGTTT TGGAACTTCA TACTATTTTG
 121 TTCTTGCAAG ACGAGTGTCA GTGATTAAAC AAAAACATAA GAATAGACGT TTTATGCGTT
 181 ACTAAAAAAA AGGAAAAATA TACCAATGGA GTTGACGAAA GTTGCTAAAA ATGGAGCTGC
 241 CGCCACGTTG GTGATGTTAA AAAATGCGCG GGATGCAAAA ATGCGACCTT TCATTGGTCC
 301 GCTCATGTTA TCCTCGTGTG AGTCTTCAAC GACATCCACA CTCCCGTCAC CTTCGTCGTC
 361 AGCTGATAAA ACGGATAATC ACGACACATT CAACTTCCTT CCTGATATGC CCGACATGCG
 421 TCGTGAAGAG GAACGTCTGA AACATTTGA TCAGTGGCCC GTTACGTTTT TGACGCCGGA
 481 ACAATTGGCC CGCAACGGAT TCTACTACCT CGGTCGCGGC GACGAAGTGT GCTGTGCTTT
 541 CTGTAAGGTA GAAATTATGA GGTGGGTCGA AGGCGACGAT CCTGCCGCCG ATCATCGGAG
 601 ATGGGCGCCC CAGTGTCCCT TTGTACGAAA ACAAATGTAT GCCAACGCTG GGGGAGAGGC
 661 GACCGCTGTC GGTAGAGACG AATGTGGGGC CAGTGCGGCC ACGCAGCCTC CCCGCATGCC
 721 CGGCCCCGTG CACGCGCGGT ACTCCACCGA GGCCGCGCGG CTCGCCACCT TCAAGGACTG
 781 GCCGAGACGT ATGCGCCAAA AACCCGAGGA ACTGGCAGAG GCCGGATTCT TCTATACAGG
 841 CCAAGGTGAC AAAACGAAAT GCTTCTATTG CGACGGAGGG CTAAAAGATT GGGAAAGCGA
 901 TGACGTTCCG TGGGAACAGC ACGCCAGATG GTTCGACCGC TGCGCGTACG TGCAATTGGT
 961 GAAAGGACGT GACTACATTC AGAAGGTGAA GTCGGAGGCC ACTGCGATAT CTGCTAGCGA
1021 AGAAGAACAG GCCGCCACCA ATGATTCGAC TAAGAACGTC GCCCAAGAGG GCGAGAAACA
1081 TTTGGATGAC TCTAAAATAT GTAAAATATG TTATTCCGAG GAGCGTAACG TGTGCTTCGT
1141 GCCGTGCGGC CACGTGGTGG CGTGCGCCAA GTGCGCGCTG TCGACGGACA AGTGCCCGAT
1201 GTGTCGCAGG ACGTTCACGA ATGCGGTGCG GCTCTACTTC TCGTGAAAGG ACCCTCCTCG
1261 CGAGCTGTAT ACTAATCACT TCACCGGGCG GCCCTGGAGC GTGCTGAAAC CACCCTTCGA
1321 ACGAAACCGC GTATCCTGTG ATTTTTACAT TAAATAAATT TACAAATTGA TAGCGGTGGG
1381 GCAATGTATA GGAACTCGTC AGAACTCGCG AGTTGACGTG CAGGAAGGAG TTAGTGATTT
1441 GTAAACTTGT AAACTGATGT TGAAATGATT TTATTTATTA TTTAAAATTC TAATGACAAA
1501 GTGTAAGTAA ATAAATGTAC ATATTATTTT AGATTATCAG TTTGTCCCAC CGACAAAAGT
1561 GAAATGTACA TAGGTGTTTT CATATCACTT CAACAGTCGA AGACCTTCTT TTTGAATTTA
1621 AGGATATATA TTTATACATA TAAATTAAAA TTTTAACGAG ACATCAATAT AAATGGTTTA
1681 ACAACTTATT TATACACTGA AATCAAGTGA AGTGTAACAT GGTCTGAAGA ATGTTTTACT
1741 GATTTCACTT CCCCTGTTGA AGTGATAAAA TTCTAATGTA AATCCAGAGT TTAAATGTCG
1801 TCATAATTAA TATAAGAAAC AAGTTTTACG CTTCTTTTGC TTGAAAAATC TTATAATTGA
1861 TTCAGGAATT ATTTAATGTG ACTATATTTT GTTCCTGTAA ATAACATAAT ATATACTATT
1921 TATTGATTAA TTCTGACATA ATTTATGGCA ATTCCGTAAG ATACAATCCA ATACTTATTT
1981 CATGTAACTC ACTTCAAAAT AGTTGAATGT GTGGTGTGAT TATAATGTTA AATGTCTAAA
2041 TTTATAATAA ATTGAGCAAA GTTGCATTTA ATGTATGAAT ACTAATTATT GTTTTAACAA
2101 AACATTTAAG TATAATCTGC TCTGTGATTT TAATGTATCA AGAAATAACC CCAACACCTT
2161 AATTGAAGTT TTTACATTGT TGCTGATAAA AAAAATCATA TCAATTACAT TTACAAGTCA
2221 ATTTTAATTG TTCAGAAACC AAACACAATT TTGTTAGTGA CTCCTGCTTT ACGAAGTAGT
2281 ATGACAAACC AGTGTTTCGT TGATTGCATT AATTTAGTTG TAACCAATAT TTACACTCAA
```

-continued

```
2341 CATTTTAAGA TGTCATTGAG GAATTCTGTA TAAAAAATGG GAATTTATTT ATTGGTGTAT

2401 AATACAATCC CGCACAAGCC ATTTGCAAGT TTCTACACAA CTAAAACGTA TTGTATCCAT

2461 TATCTATACG TCATATCATT AATATATACT TGCTTTAGCA AACATATATT CACGAATAAC

2521 TTCACAATAT ATTTTTGTAA ATCAACATAT TAATGGTAAT TAACGAATCG CACGGTACAA

2581 ATAGTGATAA CTGCTGAGTG CACTAAATAG TAAGAGAATT TATITAAACA GTCAAATTTT

2641 GTTTCATAAG TAGTTATTTC ATACTGTTGA ATGTTATTCA TTAAAACAAA TGTTAAAGCA

2701 AAAAAAAAAA AAAAAAGTCG TGACTGGGAA AA
```

BmIAP coding region nucleotide sequence:

```
   1 ATGGAGTTGA CGAAAGTTGC TAAAAATGGA GCTGCCGCCA CGTTGGTGAT GTTAAAAAAT

61 GCGCGGGATG CAAAAATGCG ACCTTTCATT GGTCCGCTCA TGTTATCCTC GTGTGAGTCT

121 TCAACGACAT CCACACTCCC GTCACCTTCG TCGTCAGCTG ATAAAACGGA TAATCACGAC

181 ACATTCAACT TCCTTCCTGA TATGCCCGAC ATGCGTCGTG AAGAGGAACG TCTGAAAACA

241 TTTGATCAGT GGCCCGTTAC GTTTTTGACG CCGGAACAAT TGGCCCGCAA CGGATTCTAC

301 TACCTCGGTC GCGGCGACGA AGTGTGCTGT GCTTTCTGTA AGGTAGAAAT TATGAGGTGG

361 GTCGAAGGCG ACGATCCTGC CGCCGATCAT CGGAGATGGG CGCCCCAGTG TCCCTTTGTA

421 CGAAAACAAA TGTATGCCAA CGCTGGGGGA GAGGCGACCG CTGTCGGTAG AGACGAATGT

481 GGGGCCAGTG CGGCCACGCA GCCTCCCCGC ATGCCCGGCC CCGTGCACGC GCGGTACTCC

541 ACCGAGGCCG CGCGGCTCGC CACCTTCAAG GACTGGCCGA GACGTATGCG CCAAAAACCC

601 GAGGAACTGG CAGAGGCCGG ATTCTTCTAT ACAGGCCAAG GTGACAAAAC GAAATGCTTC

661 TATTGCGACG GAGGGCTAAA AGATTGGGAA AGCGATGACG TTCCGTGGGA ACAGCACGCC

721 AGATGGTTCG ACCGCTGCGC GTACGTGCAA TTGGTGAAAG GACGTGACTA CATTCAGAAG

781 GTGAAGTCGG AGGCCACTGC GATATCTGCT AGCGAAGAAG AACAGGCCGC CACCAATGAT

841 TCGACTAAGA ACGTCGCCCA AGAGGGCGAG AAACATTTGG ATGACTCTAA AATATGTAAA

901 ATATGTTATT CCGAGGAGCG TAACGTGTGC TTCGTGCCGT GCGGCCACGT GGTGGCGTGC

961 GCCAAGTGCG CGCTGTCGAC GGACAAGTGC CCGATGTGTC GCAGGACGTT CACGAATGCG

1021 GTGCGGCTCT ACTTCTCGTG A
```

BmIAP polypeptide amino acid sequence:

(SEQ ID NO: 2)

```
  1 MELTKVAKNGAAATLVMLKNARDAKMRPFI

31 GPLMLSSCESSTTSTLPSPSSSADKTDNHD

61 TFNFLPDMPDMRREEERLKTFDQWPVTFLT

91 PEQLARNGFYYLGRGDEVCCAFCKVEIMRW

121 VEGDDPAADHRRWAPQCPFVRKQMYANAGG

151 EATAVGRDECGASAATQPPRMPGPVHARYS

181 TEAARLATFKDWPRRMRQKPEELAEAGFFY

211 TGQGDKTKCFYCDGGLKDWESDDVPWEQHA

241 RWFDRCAYVQLVKGRDYIQKVKSEATAISA

271 SEEEQAATNDSTKNVAQEGEKHLDDSKICK

301 ICYSEERNVCFVPCGHVVACAKCALSTDKC

331 PMCRRTFTNAVRLYFS*
```

The full-length BmIAP cDNA (SEQ ID NO:1) (Genbank accession number AF281073) contains a continuous open reading frame (ORF) encoding a protein of 346 amino acids (FIG. 1B). This ORF is initiated by an AUG within a favorable context for translation (see, e.g., Kozak (1996) Mammalian Genomes 7:563-574) and is preceded by upstream stop codons in all three reading frames. FIG. 1A shows the location of the BIR domains (BIR1, residues 74 to 140; BIR2, residues 182 to 249; of SEQ ID NO:2) and the RING domain (residues 298 to 314; of SEQ ID NO:2) of BmIAP. FIG. 1B is the full length amino acid sequence of BmIAP (SEQ ID NO:2). Sequence alignments of the BIR1 (FIG. 1C), BIR2 (FIG. 1D) and RING (FIG. 1E) domains of BmIAP with the corresponding domains of other IAP family members are shown, with bold text indicates identical amino acid. The Genbank accession numbers of sequences used for the alignments are: *Bombyx mori* IAP (BmIAP) AF281073, *Spodoptera frugiperda* IAP (SfIAP) AF186378, *Trichoplusia ni* IAP (TnIAP) AF195528, *Orgyia pseudotsugata nucleopolyhedrovirus* IAP (OpIAP) P41437, *Cydia pomonella granulovirus* IAP (CpIAP) P41436, and *Drosophila melanogaster* IAP1 (DIAP1) Q24306.

Similar to SfIAP, the BmIAP protein contains two BIR domains followed by a RING domain near its C-terminus (FIG. 1A and 1B). In the BIR domain of BmIAP, the conserved presence and spacing of cysteine and histidine residue ($CX_2CX_6WX_9HX_6C$) (SEQ ID NO:7) is also observed. Within BIR and RING regions, BmIAP shares 88% amino acid identity (92% similarity) with SfIAP, 90% identity (92% similarity) with TnIAP and 76% identity (81% similarity) with CpIAP (FIG. 1C-1E). Thus BmIAP shares high sequence sequence similarity with the other two lepidopteran IAPs, SfIAP and TnIAP, suggesting evolutionary conservation.

Figure 2:
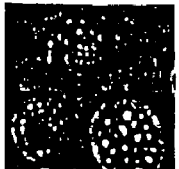
FIG. 2 is a representation of photographs of Sf-21 cells taken three days post-transfection at 40× magnification; the cells were co-transfected with p35-deficient AcMNPV viral DNA and (FIG. 2A) BmIAP, or (FIG. 2D) SfIAP, (the production of occlusion bodies is indicated by arrowheads)
Figure 2:
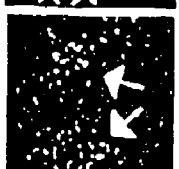
Figure 2:
Figure 2:
Figure 2:
Figure 2:

Experiments demonstrated that both BIR and RING domains of BmIAP are required to block apoptosis induced by apoptosis suppressor p35-deficient AcMNPV virus. The anti-apoptotic activity of BmIAP in insect cells was tested by co-transfecting AcMNPV p35-deficient viral DNA into Sf-21 cells with plasmids containing full-length BmIAP (SEQ ID NO:2) or truncation mutants of BmIAP lacking two BIR domains or the RING domain (see FIG. 1A). Cells expressing IAPs/IAP fragments with anti-apoptotic activity support virus replication, whereas cells without a functional IAP are unable to support virus replication and undergo apoptosis. Production of viable viral progeny from rescued viruses results in the formation of occlusion bodies, serving as a convenient end-point. Occlusion body formation serves as a visual screening end-point under light-microscopy, as described by Crook (1993) J. of Virol. 67:2168-2174; Birnbaum (1994) J. of Virol. 68:2521-2525. Sf-21 cells co-transfected with p35-deficient AcMNPV viral DNA and (FIG. 2A) BmIAP, or (FIG. 2D) SfIAP, show the production of occlusion bodies as indicated by arrowheads, whereas (FIG. 2B) BmIAP-BIR, (FIG. 2C) BmIAP-RING, and (FIG. 2E) AcIAP show apoptotic body formation (indicated by arrowheads) without occlusion body formation. Since SfIAP has been shown to block apoptosis in both insect and mammalian cells (see, e.g., Huang (2000) supra), whereas AcIAP is ineffective (Clem (1994) Mol. Cell. Biol. 14:5212-5222; Huang (2000) supra, SfIAP and AcIAP were used as positive and negative controls, respectively (FIGS. 2D and E). FIG. 2F is the mock transfection control.

A plasmid encoding the full-length BmIAP (SEQ ID NO:2) was able to complement the p35 (apoptosis inhibiting)-deficiency in the baculovirus, supporting occlusion body production and virus replication at 3 days post-transfection (FIG. 2A). In contrast, neither the BIR nor RING domain deletion mutants of BmIAP (see FIG. 1A) was able to support occlusion body formation (thus, no apoptosis inhibiting activity). Sf-21 cells displayed morphological changes of apoptosis, such as apoptotic body formation, when either the BIR or RING domain deletion mutants were co-transfected with p35-deficient viral DNA (FIGS. 2B and C). These results demonstrate that both the BIR and RING domain regions of BmIAP (BIR1, residues 74 to 140; BIR2, residues 182 to 249; of SEQ ID NO:2) and the RING domain (residues 298 to 314; of SEQ ID NO:2) are required in combination for the anti-apoptotic function in insect cells.

Experiments demonstrated that BmIAP inhibited Bax-induced but not Fas-induced apoptosis in mammalian cells (i.e., BmIAP protects mammalian cells against Bax-induced but not Fas-induced apoptosis). Expression plasmid encoding Bax (FIG. 3A) or Fas (FIG. 3B) were co-transfected into HEK 293 cells with the indicated myc-tagged IAP expression plasmids. Percentage apoptosis was measured 24 to 36 hours post-transfection by 4'-6-diamidino-2-phenylindole (DAPI) staining (mean+/−S.D., n=3). Recombinant BmIAP (2 uM) was added to cytosolic extracts (10 mg/ml) from HEK293 cells concurrently with the addition of 1 uM cytochrome-c/10 mM dATP. After incubation at 30° C. for 10 minutes, aliquots were withdrawn and assayed for caspase activity, as measured by release of AFC from Ac-DEVD-AFC substrate (100 uM). Data are presented in FIG. 3C as a percentage relative to control reaction in which cytochrome-c/dATP were added alone.

Figure 3:
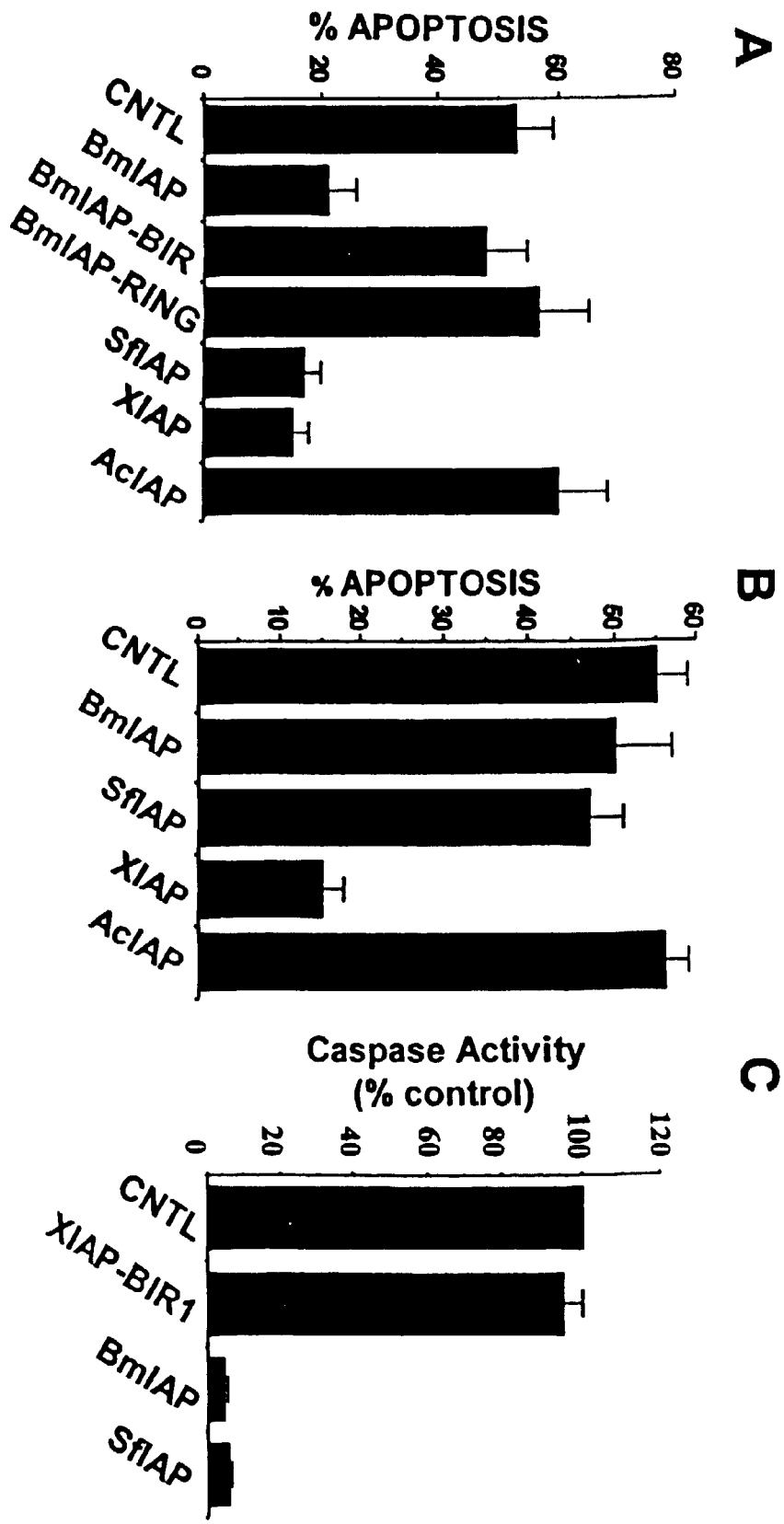
FIG. 3 schematically summarizes the results of experiments showing that recombinantly expressed BmIAP protects mammalian cells against Bax-induced but not Fas-induced apoptosis. Expression plasmid encoding Bax (FIG. 3A) or Fas (FIG. 3B) were co-transfected into HEK 293 cells with various myc-tagged IAP expression plasmids.

SfIAP and baculoviral IAPs were previously shown to block apoptosis in mammalian cells (Huang (2000) supra; Hawkins (1996) Proc. Natl. Acad. Sci. USA 93:13786-13790; Uren (1996) Proc. Natl. Acad. Sci. USA 93:4974-4978; Hawkins (1998) Cell Death and Differentiation 5:569-576). To explore whether BmIAP has similar properties, we co-expressed BmIAP in HEK293 cells with either Fas or Bax, representing two major pathways that utilize caspase-8 and caspase-9, respectively, as their apical proteases. Similar to SfIAP, full-length BmIAP (SEQ ID NO:2) inhibited Bax (FIG. 3A) but not Fas-induced apoptosis (FIG. 3B). In contrast human XIAP protected cells against both Bax and Fas-induced apoptosis. As in Sf-21 cells, the inhibition of Bax-induced apoptosis in mammalian cells also requires both the BIR and RING domains of BmIAP (SEQ ID NO:2) (see FIG. 1A), suggesting the conservation of the structural requirements for inhibition (FIG. 3A). Immunoblot analysis indicated that the levels of the BIR and RING truncation proteins were similar to that of full-length BmIAP in transfected cells, excluding differences in protein levels as an explanation for the failure of the BIR domains or RING domain to suppress cell death.

Figure 4:
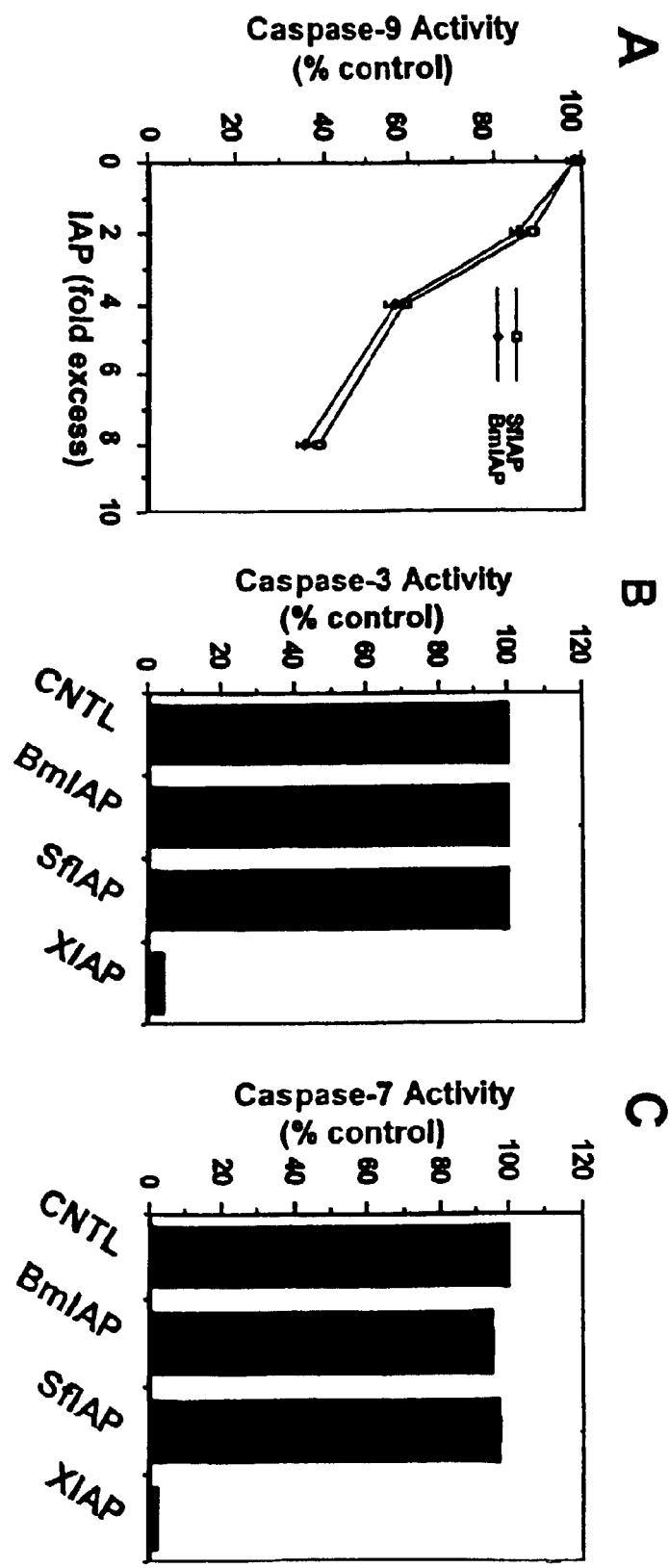
FIG. 4 schematically summarizes the results of experiments showing that recombinant BmIAP directly suppresses caspase-9 but not caspase-3 or caspase-7.

These results were further confirmed in a cell-free system in which exogenously added cytochrome-c, an agonist of the caspase-9 activating protein Apaf-1 (see, e.g., Zou (1997) Cell 90:405-413), induced activation of caspase-3 and similar effector proteases. BmIAP directly suppressed caspase-9, but not caspase-3 or caspase-7. This was measured by hydrolysis of Ac-DEVD-AFC, as described by Quan (1995) J. Biol. Chem. 270:10377-10379). Recombinant active (FIG. 4A) caspase-9 was added at 0.2 uM and incubated at 37° C. with Ac-LEHD-AFC substrate (100 uM) in the presence or absence of various concentration (0.2-1.6 uM) of recombinant purified BmIAP or SfIAP. AFC release was measured continuously. In FIG. 4, data are expressed as a percentage relative to control reactions lacking IAPs, using rates determined from the linear portion of enzyme progress curves. Various control GST-fusion proteins had no inhibition effect.

Recombinant caspase-3 (2.6 nM) was incubated at 37° C. with Ac-DEVD-AFC substrate (100 uM) in the presence or absence of 0.05 uM GST-XIAP, 0.5 uM GST-BmIAP (200 fold molar excess to caspase) or 0.5 uM GST-SfIAP (200 molar excess) (FIG. 4B). AFC release was measured as above.

Recombinant caspase-7 (7.0 nM) was incubated at 37° C. with Ac-DEVD-AFC substrate (100 uM) in the presence or absence of 0.14 uM GST-XIAP, 0.7 uM GST-BmIAP (100 fold molar excess relative to caspase or 0.7 uM GST-SfIAP (100 molar excess) (FIG. 4C). AFC release was measured as above. In cytosolic extracts treated with cytochrome-c, recombinant BmIAP and positive control recombinant SfIAP completely blocked the hydrolysis of Ac-DEVD-AFC whereas negative control recombinant XIAP-BIR1 had no effect on caspase activity (FIG. 4C). Since caspases-3 and -7 are common to both Bax and Fas pathways, these results demonstrate that BmIAP, like SfIAP, inhibits the mitochondria/cytochrome-c pathway in mammalian cells, thus, suppressing apoptosis at a step upstream of caspases-3 and -7. This finding is supported by the observation that BmIAP does not inhibit caspases-3 and -7 in vitro.

These experiments demonstrated that BmIAP is a direct inhibitor of caspase-9. Purified recombinant BmIAP was incubated with purified recombinant caspase-9. Residual activity was measured using Ac-LEHD-AFC as a substrate of caspase-9. BmIAP inhibited recombinant caspase-9 in a concentration-dependent manner. The relative amount of BmIAP required for caspase-9 inhibition was about 8 fold molar excess (FIG. 4A), similar to the results reported previous for SfIAP and XIAP (Deveraux (1999) supra; Huang (2000) supra; SfIAP was shown to directly inhibit caspase-9). Unlike XIAP, but similar to SfIAP, BmIAP did not inhibit recombinant caspase-3 and caspase-7 (caspases-3, -7 and -9 are involved in apoptotic pathway induced by Bax), suggesting a narrower range of caspases specificity compared to human XIAP (FIGS. 4B and C).

A number of embodiments of the invention have been described. Nevertheless, it will be understood that various modifications may be made without departing from the spirit and scope of the invention. Accordingly, other embodiments are within the scope of the following claims.

What is claimed is:

1. A transgenic plant comprising a nucleic acid encoding a polypeptide having at least 95% sequence identity to SEQ ID NO:2, wherein said polypeptide is capable of inhibiting caspase 9.

2. The transgenic plant of claim 1, wherein the polypeptide is capable of inhibiting Bax-induced apoptosis in *Spodoptera frugiperda* or *Bombyx mori* cells.

3. The transgenic plant of claim 1, wherein the polypeptide is capable of inhibiting Bax-induced apoptosis in mammalian cells.

4. The transgenic plant of claim 1, wherein the nucleic acid encodes a polypeptide capable of inhibiting apoptosis.

5. The transgenic plant of claim 1, wherein the plant is abiotic or biotic insult resistant.

6. The transgenic plant of claim 5, wherein the biotic insult is induced by a plant pathogen.

7. The transgenic plant of claim 6, wherein the plant pathogen is a virus, a fungus, a bacteria or a nematode.

8. The transgenic plant of claim 5, wherein the abiotic insult is induced by high moisture, low moisture, salinity, nutrient deficiency, air pollution, high temperature, low temperature, soil toxicity, herbicides or insecticides.

9. The transgenic plant of claim 1, wherein at least a portion of the plant exhibits a decreased level of senescence.

10. The transgenic plant of claim 1, wherein the polypeptide comprises a BIR1 domain having the amino acid sequence of residues 74 to 140 of SEQ ID NO:2, BIR2 domain having the amino acid sequence of residues 182 to 249 of SEQ ID NO:2, and a RING domain having the amino acid sequence of residues 298 to 314 of SEQ ID NO:2.

11. The transgenic plant of claim 1, wherein the polypeptide is capable of inhibiting apoptosis involving caspase 9 in a plant cell.

12. The transgenic plant of claim 1, wherein the polypeptide is capable of inhibiting apoptosis involving caspase 9 in a cell of the plant.

13. The transgenic plant of claim 5, wherein the abiotic or biotic insult involves apoptosis, wherein the apoptosis involves caspase 9.

14. A transgenic plant comprising a nucleic acid encoding a polypeptide comprising SEQ ID NO:2.

15. A transgenic plant comprising a nucleic acid comprising SEQ ID NO:1.

16. A transgenic plant comprising a expression cassette comprising at least one nucleic acid operably linked to a promoter, wherein the nucleic acid encodes a polypeptide having at least 95% sequence identity to SEQ ID NO:2, wherein said polypeptide is capable of inhibiting caspase 9.

17. The transgenic plant of claim 16, wherein the promoter is a constitutive promoter.

18. The transgenic plant of claim 16, wherein the promoter is a developmentally regulated or a tissue specific promoter.

19. The transgenic plant of claim 16, wherein the polypeptide comprises SEQ ID NO:2.

20. A seed capable of germinating into a plant having in its genome a heterologous nucleic acid sequence encoding a polypeptide having at least 95% sequence identity to SEQ ID NO:2, wherein said polypeptide is capable of inhibiting caspase 9.

21. The seed of claim 20, wherein the nucleic acid encodes a polypeptide capable of inhibiting apoptosis in a plant cell.

22. A method for inhibiting apoptosis in a plant comprising the following steps: (a) providing an isolated or recombinant nucleic acid comprising a sequence encoding a polypeptide having at least 95% sequence identity to SEQ ID NO:2, wherein said polypeptide is capable of inhibiting caspase 9, wherein the nucleic acid encodes polypeptide capable of inhibiting apoptosis in a plant, and (b) contacting the nucleic acid with the plant and expressing the nucleic acid to produce an amount of polypeptide sufficient to inhibit apoptosis in the plant.

* * * * *

UNITED STATES PATENT AND TRADEMARK OFFICE
CERTIFICATE OF CORRECTION

PATENT NO. : 7,786,347 B2
APPLICATION NO. : 11/623637
DATED : August 31, 2010
INVENTOR(S) : Q. Huang et al.

It is certified that error appears in the above-identified patent and that said Letters Patent is hereby corrected as shown below:

On the Patent Cover item (73) Assignee, please add the following on the line following "Burnham Institute for Medical Research, La Jolla, CA (US)":

The Regents of the University of California, Oakland, CA (US)

Signed and Sealed this
Twenty-sixth Day of April, 2011

David J. Kappos
*Director of the United States Patent and Trademark Office*